US008698644B2

(12) United States Patent
Okubo

(10) Patent No.: US 8,698,644 B2
(45) Date of Patent: Apr. 15, 2014

(54) SAMPLE PROCESSING APPARATUS, SAMPLE CONTAINER TRANSPORTING APPARATUS, SAMPLE PROCESSING METHOD AND SAMPLE CONTAINER TRANSPORTING METHOD

(75) Inventor: Koichi Okubo, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 402 days.

(21) Appl. No.: 13/165,093

(22) Filed: Jun. 21, 2011

(65) Prior Publication Data

US 2011/0316713 A1 Dec. 29, 2011

(30) Foreign Application Priority Data

Jun. 25, 2010 (JP) ................................. 2010-144970

(51) Int. Cl.
*G08B 21/00* (2006.01)

(52) U.S. Cl.
USPC .......................................... 340/673; 340/674

(58) Field of Classification Search
USPC ........................................................ 340/673
See application file for complete search history.

(56) References Cited

U.S. PATENT DOCUMENTS

| 7,443,298 | B2 * | 10/2008 | Cole et al. .................. 340/572.4 |
| 8,194,235 | B2 * | 6/2012 | Kosaka et al. ................... 356/39 |
| 2003/0180138 | A1 * | 9/2003 | Scheltes et al. ............ 414/788.7 |
| 2004/0208787 | A1 | 10/2004 | Takahashi et al. |
| 2007/0188318 | A1 * | 8/2007 | Cole et al. ................. 340/539.13 |
| 2008/0235102 | A1 * | 9/2008 | Harris et al. .................... 705/23 |
| 2012/0192660 | A1 * | 8/2012 | Hajrovic et al. ........... 73/863.01 |

FOREIGN PATENT DOCUMENTS

| JP | 10-019899 | 1/1998 |
| JP | 11-083863 A | 3/1999 |

* cited by examiner

*Primary Examiner* — Travis Hunnings
(74) *Attorney, Agent, or Firm* — Brinks Gilson & Lione

(57) ABSTRACT

The present invention is a sample processing apparatus including: a sample processing unit configured to process a sample contained in a sample container; one or more detectors located to detect the sample container both before and after the sample contained therein is processed by the sample processing unit; and a controller configured to perform an operation to alert a user if the one or more detectors fail to detect the sample container after the sample processing unit processed the sample in the sample container.

20 Claims, 20 Drawing Sheets

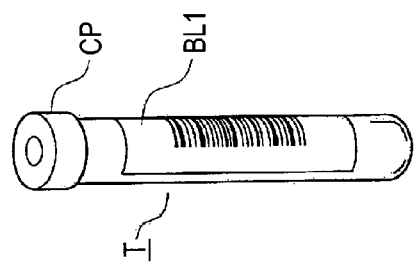
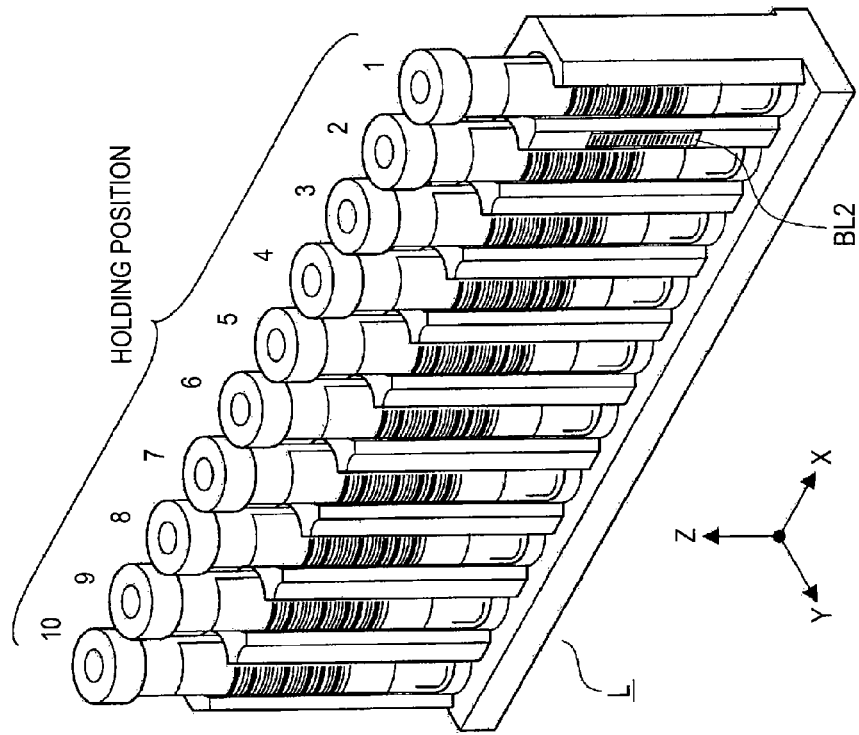

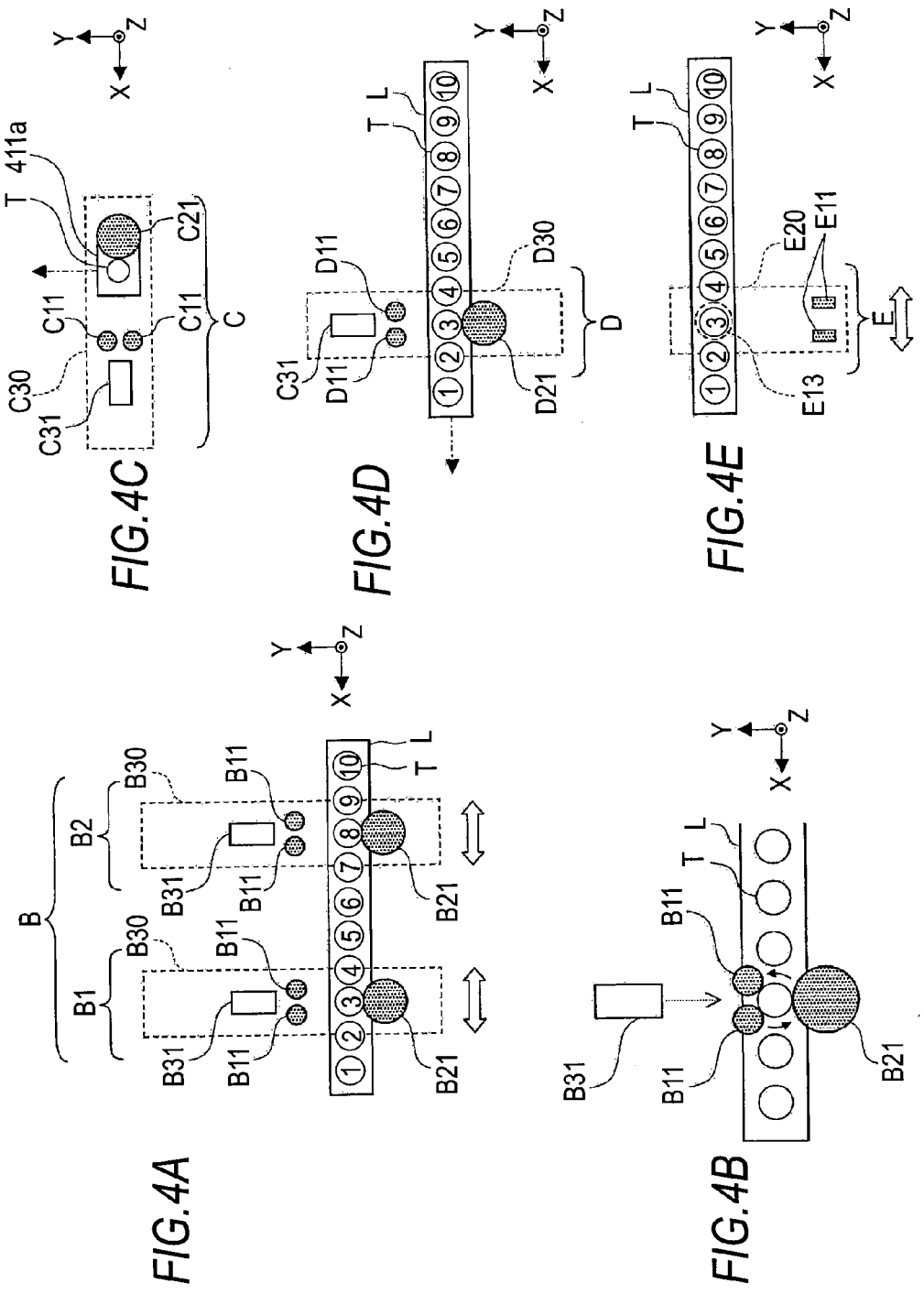

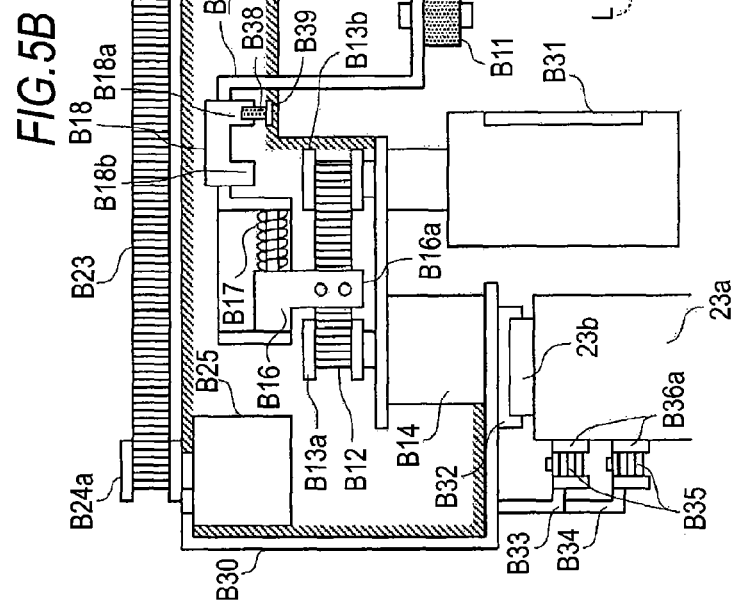
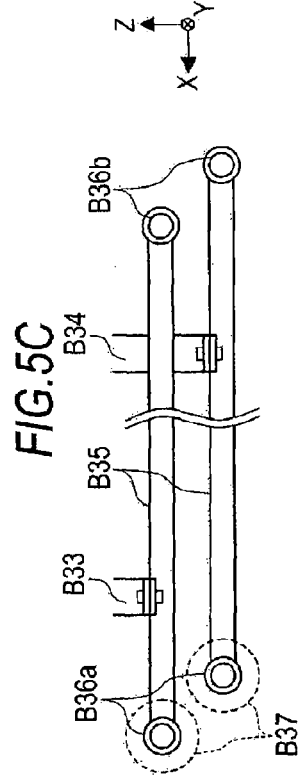
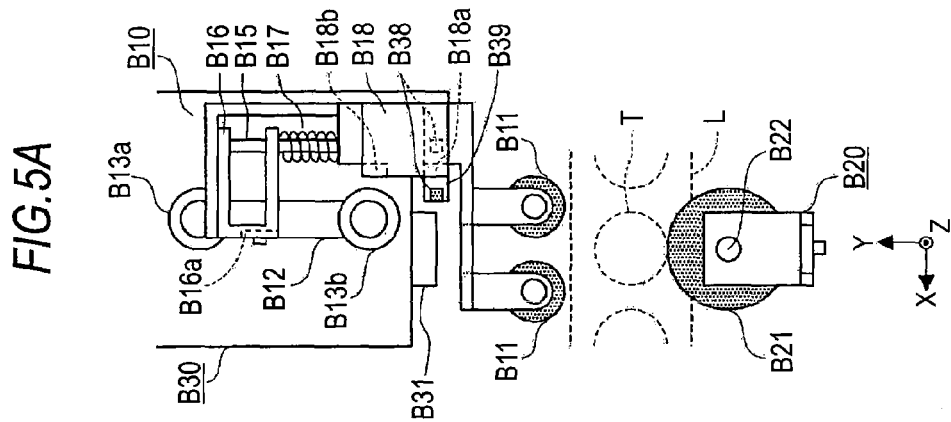

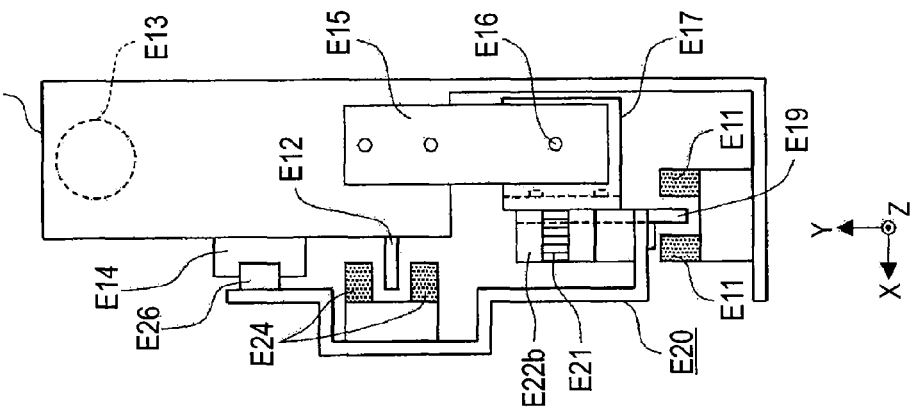
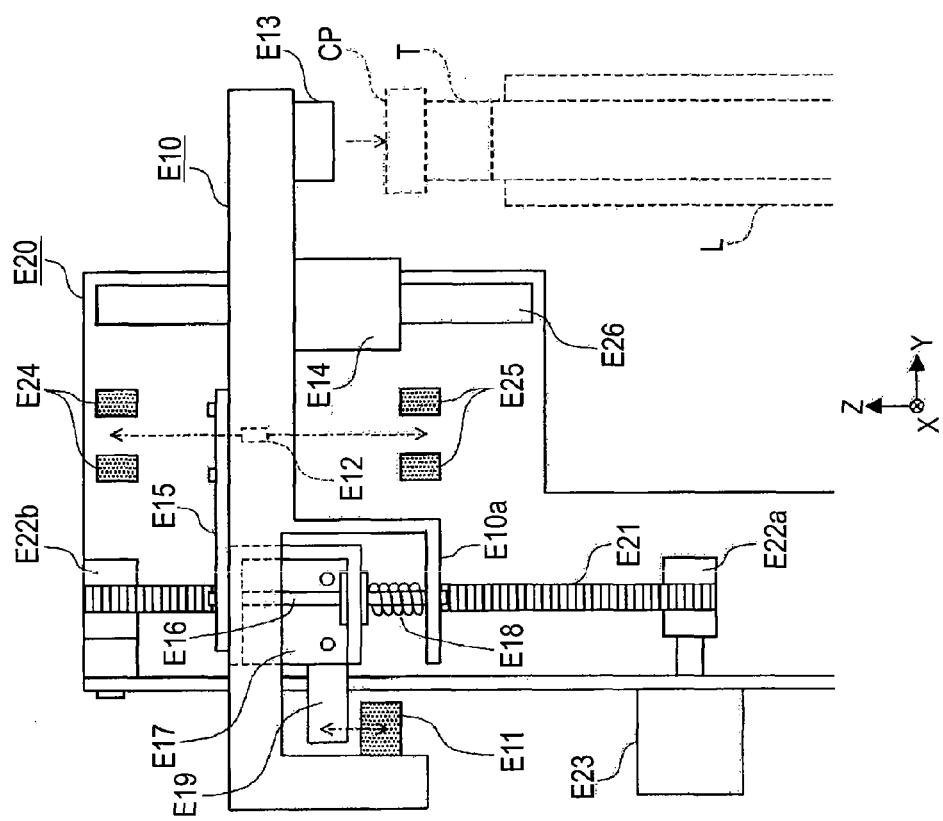

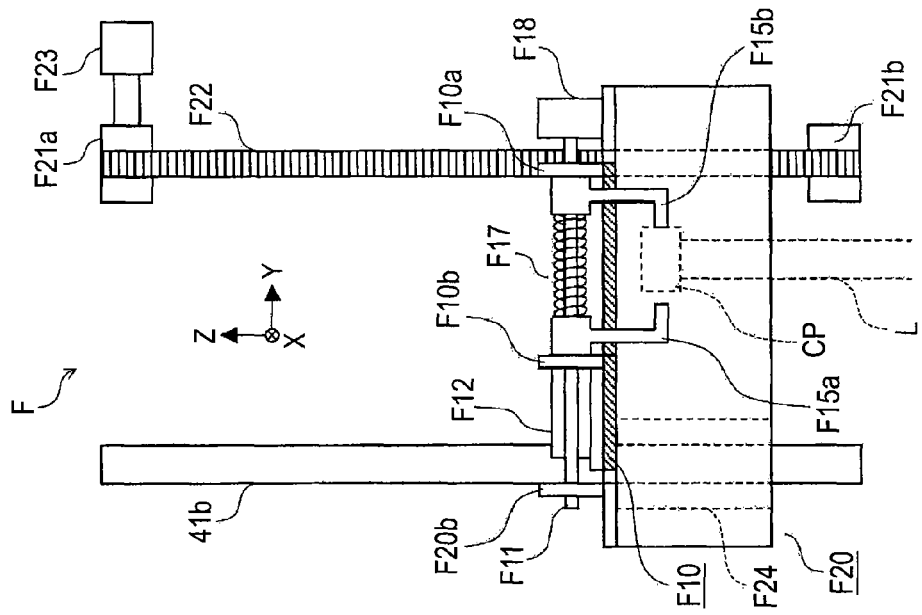
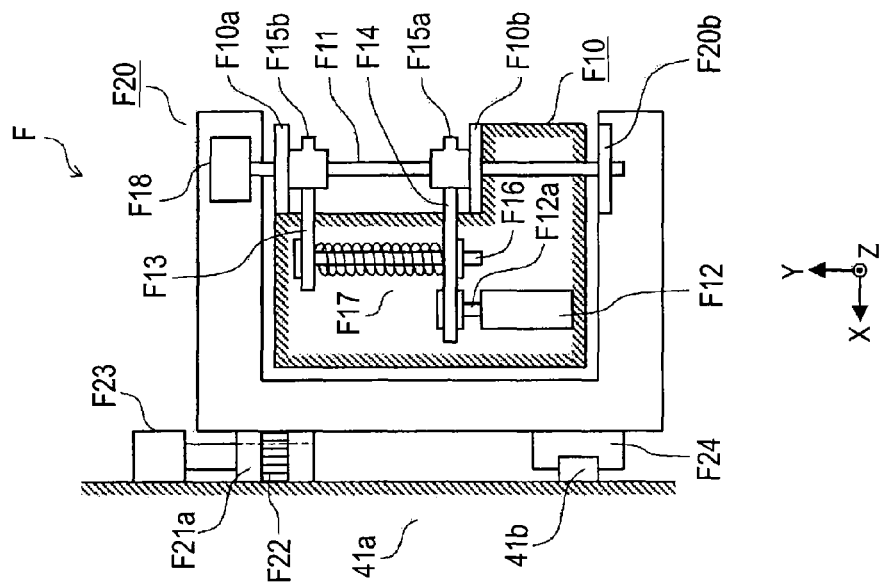

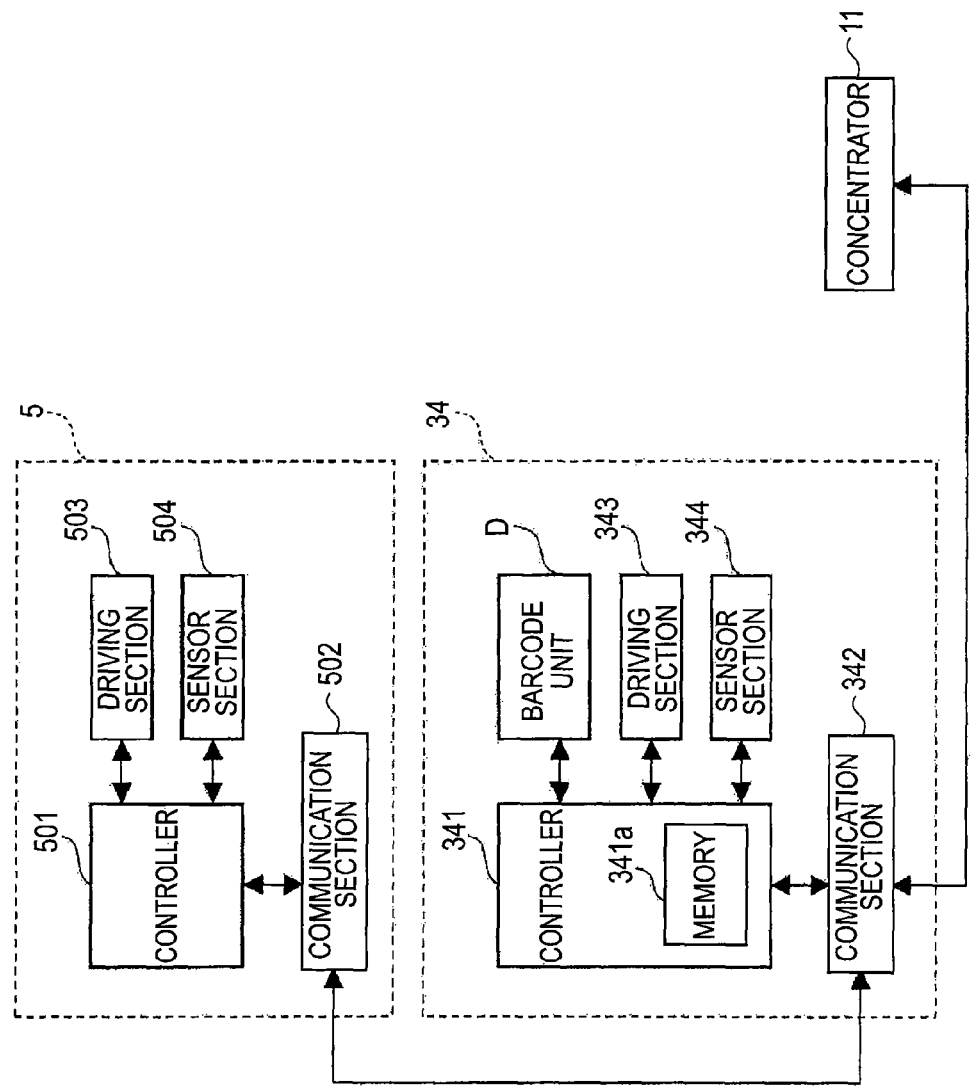

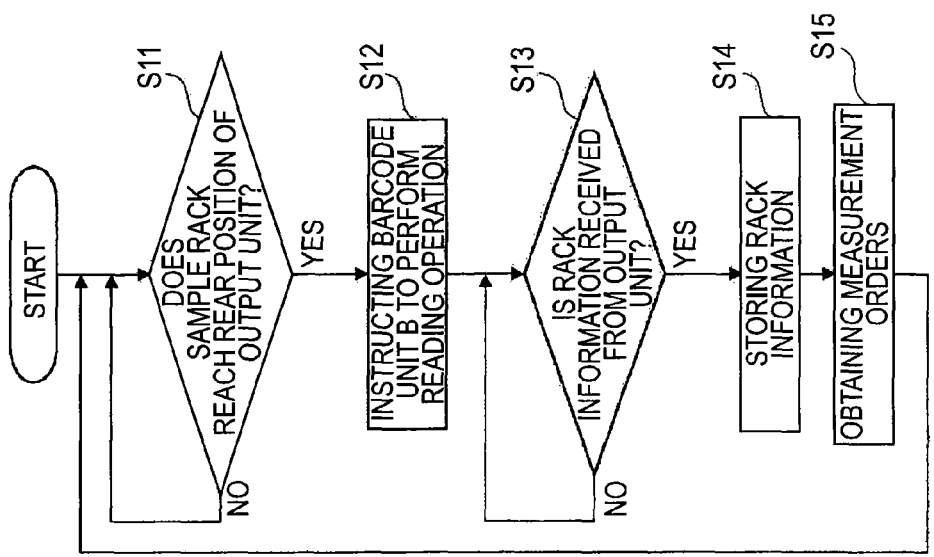

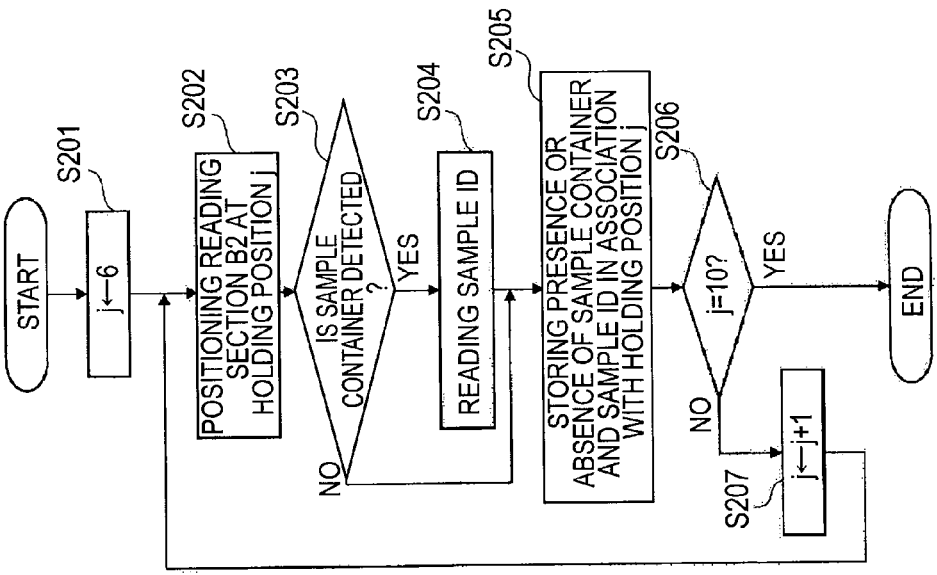
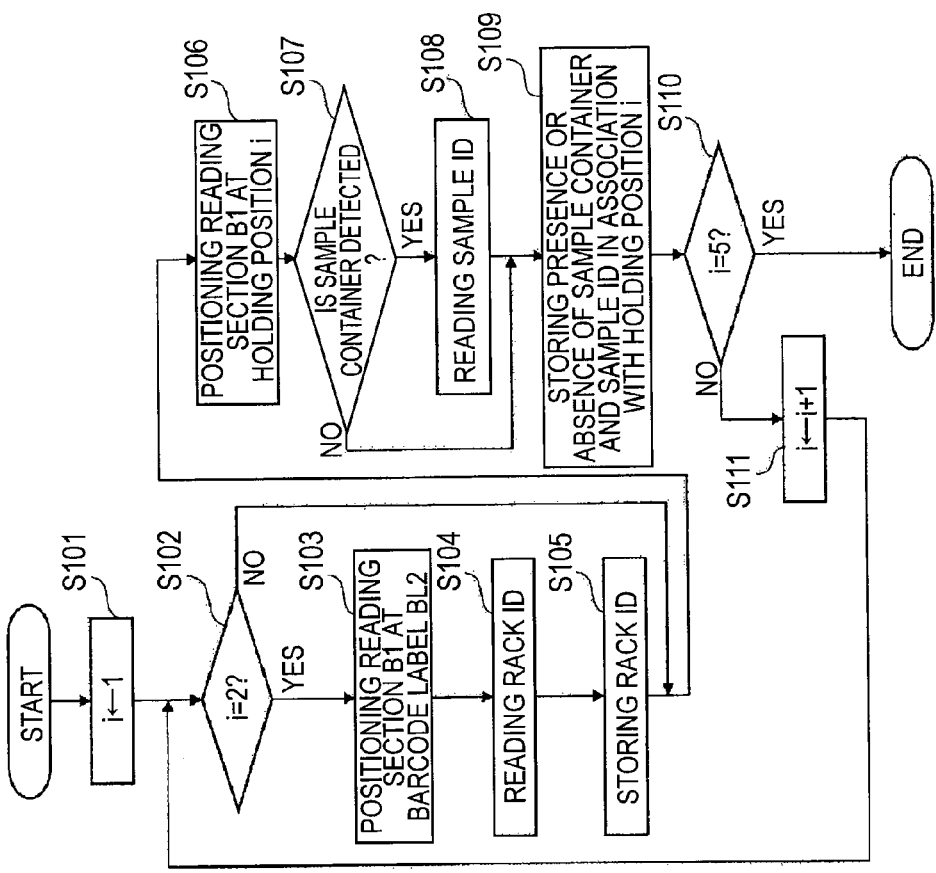

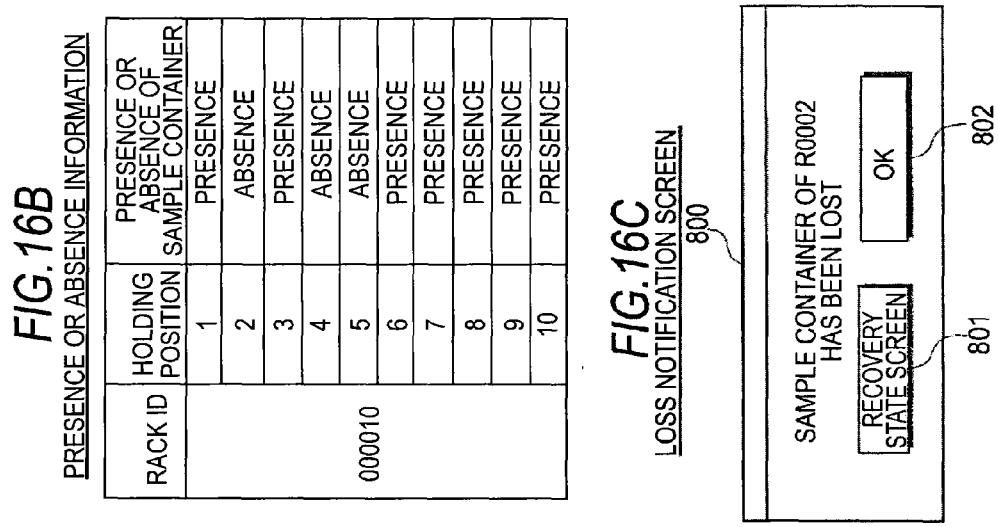
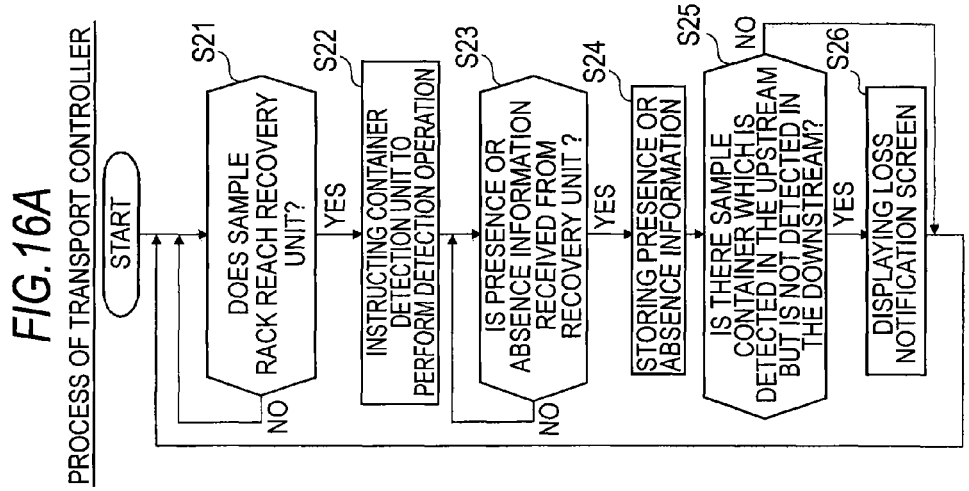

FIG.18A

PROGRESS STATE SCREEN

| SAMPLE ID | DATE AND TIME OF BARCODE READING IN OUTPUT UNIT | STATE | STORAGE DATE AND TIME |
|---|---|---|---|
| R0001 | 2010/01/15 10:10 | STORED | 2010/01/15 10:10 |
| R0002 | 2010/01/15 10:10 | NOT CLEAR | |
| ... | ... | ... | ... |
| R0021 | 2010/01/15 10:20 | DURING PROCESSING | |
| ... | ... | ... | ... |

FIG.18B

RECOVERY STATE SCREEN

| RACK ID | SAMPLE CONTAINER RECOVERY STATE |
|---|---|
| 000001 | ○ ○ ○ ○ ○ ○ ○ ○ ○ ○ |
| 000002 | ○ ○ ○ ○ ○ ○ ○ ○ ○ ○ |
| ... | ... |
| 000010 | ○ ○ ⊙ ○ ○ ○ ○ ○ ○ ○ |
| ... | ... |

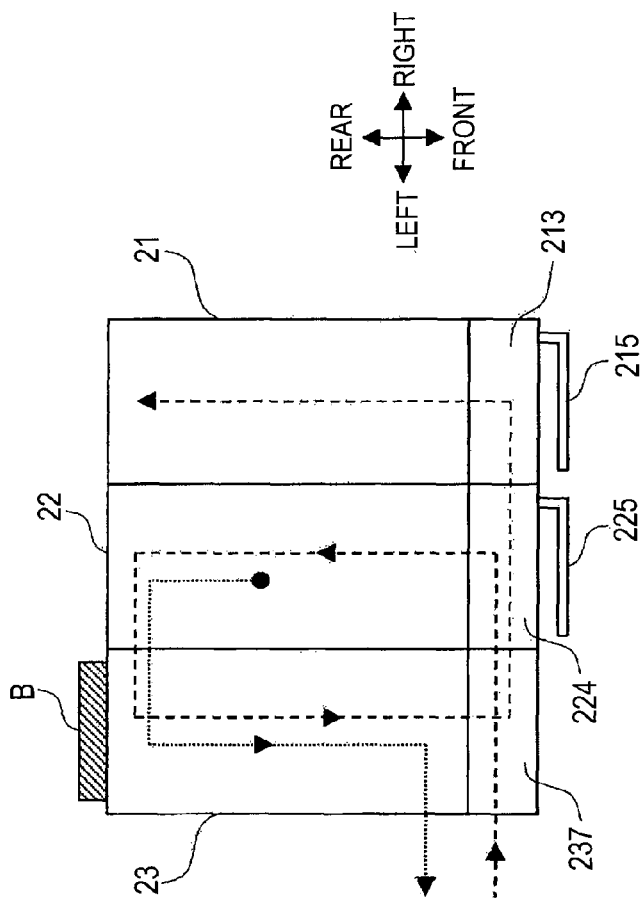
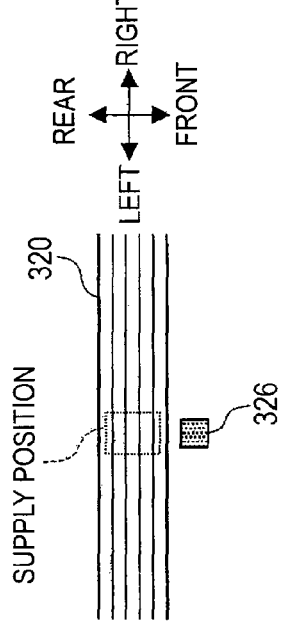
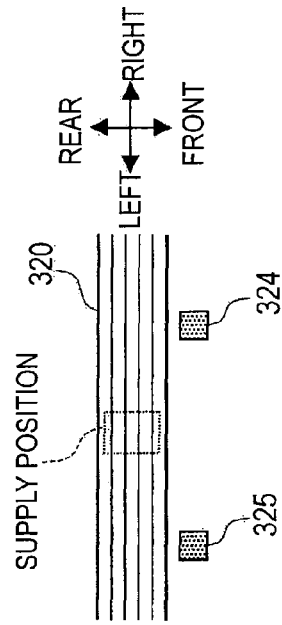

SAMPLE PROCESSING APPARATUS, SAMPLE CONTAINER TRANSPORTING APPARATUS, SAMPLE PROCESSING METHOD AND SAMPLE CONTAINER TRANSPORTING METHOD

RELATED APPLICATIONS

This application claims priority under 35 U.S.C. §119 to Japanese Patent Application No. 2010-144970 filed on Jun. 25, 2010, the entire content of which is hereby incorporated by reference.

BACKGROUND OF THE INVENTION

1. Field of the Invention

The present invention relates to a sample processing apparatus which processes a sample in a sample container, a sample processing method for the sample processing apparatus, a sample container transporting apparatus which transports a sample container, and a sample container transporting method for the sample container transporting apparatus.

2. Description of the Related Art

Hitherto, there have been known systems which transport a sample container containing a sample such as blood or urine by a transport section and execute processes such as centrifugation and measurement.

For example, in Japanese Laid-Open Patent Publication No. H11-83863, there is a disclosure of a system which includes: a feeding unit in which a rack storing sample containers is placed; a transport section which transports a rack fed from the feeding unit; a sample processing unit which fetches a rack from the transport section and performs processes such as centrifugation, opening and dispensing; a storing section which stores a rack returning to the transport section from the sample processing unit; and a central processing section. In this system, a plurality of sensors for detecting a rack is disposed and the central processing section is configured to display a location screen showing the position of a rack in the system on a monitor. In addition, the central processing section is configured to retrieve, when information necessary for sample retrieval is input, a corresponding sample and display the sample on the location screen in order for the sample to be able to be identified at first glance.

In the system which transports a sample container to process a sample, the sample container may be lost in the course of transport of the sample container or the sample processing. However, in the system described in Japanese Laid-Open Patent Publication No. H11-83863, it is difficult for a user to rapidly notice the loss of the sample container. Accordingly, it is difficult for the user to rapidly perform necessary processes such as a search for the lost sample container and re-examination of the sample.

SUMMARY OF THE INVENTION

The scope of the invention is defined solely by the appended claims, and is not affected to any degree by the statements within this summary.

A first aspect of the present invention is a sample processing apparatus comprising: a sample processing unit configured to process a sample contained in a sample container; one or more detectors located to detect the sample container both before and after the sample contained therein is processed by the sample processing unit; and a controller configured to perform an operation to alert a user if the one or more detectors fail to detect the sample container after the sample processing unit processed the sample in the sample container.

A second aspect of the present invention is a sample container transporting apparatus for transporting a sample container to a sample processing apparatus for processing a sample in the sample container, comprising: a transport unit configured to transport the sample container from a first position to a second position; a first detector located to detect the sample container at the first position; a second detector located to detect the sample container transported to the second position; and a controller configured to perform an operation to alert a user if the second detector fails to detect the sample container which was detected by the first detector.

A third aspect of the present invention is a sample processing method comprising: (a) performing an operation of detecting a sample container containing a sample; (b) processing the sample contained in the sample container detected in the step (a); (c) performing an operation of detecting the sample container after the step (b); and (d) performing an operation to alert a user if the step (c) fails to detect the sample container which was detected in the step (a).

A fourth aspect of the present invention is a sample container transporting method of transporting a sample container to a sample processing apparatus for processing a sample in the sample container, comprising: (a) performing an operation of detecting a sample container at a first position; (b) transporting the sample container to a second position from the first position by a transport unit; (c) performing an operation of detecting the sample container transported to the second position; and (d) performing an operation to alert a user if the step (c) fails to detect the sample container which was detected in the step (a).

BRIEF DESCRIPTION OF THE DRAWINGS

FIG. 2A is a view showing the configuration of a sample container according to the embodiment;

FIG. 2B is a view showing the configuration of a sample rack according to the embodiment;

FIGS. 4A to 4E are views explaining operations of barcode units and a container detection unit according to the embodiment;

FIGS. 5A to 5C are views showing the configuration of the barcode unit according to the embodiment in detail;

FIGS. 6A and 6B are views showing the configuration of the container detection unit according to the embodiment in detail;

FIGS. 9A and 9B are views showing the configuration of a gripping unit according to the embodiment in detail.

FIG. 13 is a view showing an outline of the configurations of a transport unit and a smear preparation apparatus according to the embodiment;

FIG. 14A is a flowchart showing a process of the transport controller in the reading operation of the barcode unit B according to the embodiment;

FIG. 14B is a view conceptually showing an example of rack information;

FIGS. 15A and 15B are flowcharts showing processes of the output unit in the reading operation of the barcode unit B according to the embodiment;

FIG. 16A is a flowchart showing a process of the transport controller in the detection operation of the container detection unit E according to the embodiment;

FIG. 16B is a view conceptually showing an example of presence or absence information;

FIG. 16C is a view showing an example of a loss notification screen which is displayed on a display section;

FIG. 18A is a view showing an example of the display of a progress state screen which is displayed on the display section according to the embodiment;

FIG. 18B is a view showing an example of a recovery state screen which is displayed on the display section according to the embodiment;

FIG. 19A is a view schematically showing a sample rack transport route in a modified example according to the embodiment;

FIGS. 19B and 19C are plan views when reflection type sensors disposed near a supply position of the transport unit are viewed from the upper side in the modified example according to the embodiment.

DETAILED DESCRIPTION OF THE PREFERRED EMBODIMENTS

This embodiment relates to a sample processing system for performing examination and analysis related to blood to which the invention is applied. The sample processing system according to this embodiment includes three measuring units and one smear preparation apparatus. In the three measuring units, blood analysis is performed in parallel, and when it is necessary to prepare a smear on the basis of the analysis result, the smear preparation apparatus prepares a smear.

Hereinafter, the sample processing system according to this embodiment will be described with reference to the drawings.

Figure 1:
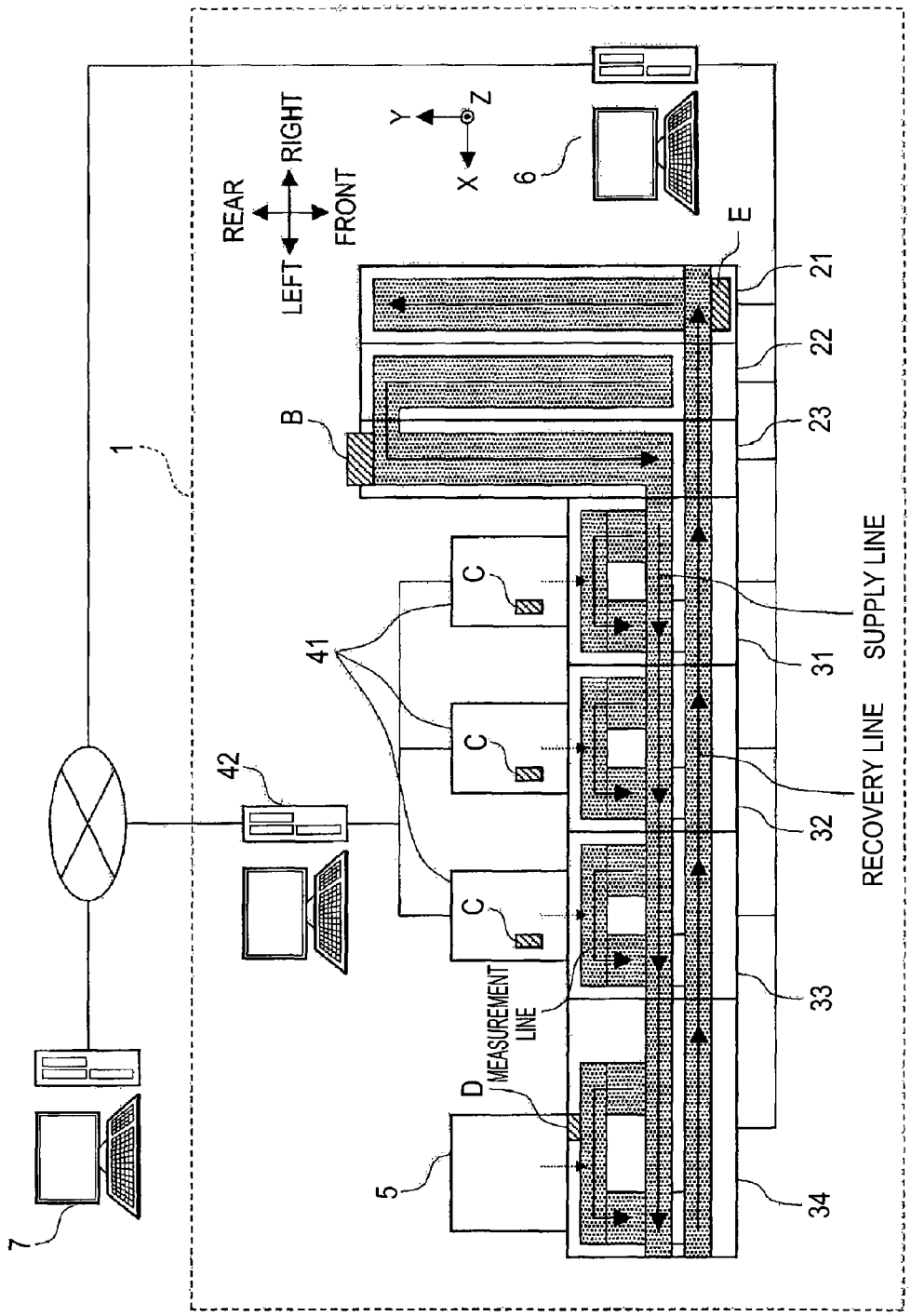
FIG. 1 is a plan view schematically showing the configuration when a sample processing system according to an embodiment is viewed from the upper side.

FIG. 1 is a plan view schematically showing the configuration when a sample processing system 1 is viewed from the upper side. The sample processing system 1 according to this embodiment includes a recovery unit 21, a feeding unit 22, an output unit 23, transport units 31 to 34, three measuring units 41, an information processing unit 42, a smear preparation apparatus 5, and a transport controller 6. In addition, the sample processing system 1 according to this embodiment is connected to a host computer 7 via a communication network so as to communicate therewith. Hereinafter, the X-axis positive direction is called the leftward direction, the X-axis negative direction is called the rightward direction, the Y-axis positive direction is called the rearward direction, the Y-axis negative direction is called the frontward direction, the Z-axis positive direction is called the upward direction, and the Z-axis negative direction is called the downward direction.

The recovery unit 21, the feeding unit 22, and the output unit 23 are each configured so that a plurality of sample racks L capable of holding ten containers T therein can be placed.

FIG. 2A is a perspective view showing the appearance of a sample container T. FIG. 2B is a perspective view showing the appearance of a sample rack L holding ten sample containers T. In FIG. 2B, the directions (the coordinate axes in FIG. 1) when the sample rack L is placed in the feeding unit 22 are also shown.

Referring to FIG. 2A, the sample container T is a tubular container made of glass or a synthetic resin having translucency and the upper end thereof is opened. A blood sample collected from a patient is contained therein and the opening at the upper end is sealed by a cap section CP. A barcode label BL1 is adhered to the side surface of the sample container T. A barcode showing a sample ID is printed on the barcode label BL1.

Referring to FIG. 2B, in the sample rack L, ten holding sections are formed at holding positions 1 to 10 as shown in the drawing so as to hold ten sample containers T in parallel in a vertical state (erect state). In addition, as shown in the drawing, a barcode label BL2 is adhered to a side surface in the Y-axis positive direction of the sample rack L. A barcode showing a rack ID is printed on the barcode label BL2.

Returning to FIG. 1, the recovery unit 21 accommodates sample racks L which are recovered through a recovery line to be described later. In addition, the recovery unit 21 detects whether or not a sample container T is held in each holding position in a sample rack L which is recovered (presence or absence of the sample container T) by a container detection unit E. In addition, the recovery unit 21 reads the rack ID of a sample rack L which is recovered by a barcode reader 243 to be described later.

The feeding unit 22 accommodates sample racks L which are fed by a user and outputs the accommodated sample racks L to the output unit 23. When sample measurement is started, first, the user sets a sample container T containing a sample in a sample rack L and places this sample rack L in the feeding unit 22. Then, this sample rack L is transported to the unit (device) on the downstream side (left side) and the measurement is performed.

The output unit 23 reads the rack ID of a sample rack L output from the feeding unit 22 and the sample IDs of sample containers T each associated with a holding position in the sample rack L by a barcode unit B, and detects the presence or absence of the sample container T in each holding position in this sample rack L. Then, the output unit 23 transmits the information read by the barcode unit B and the detected information to the transport controller 6, and outputs the sample rack L in which the reading and the detection have been completed to the transport unit 31.

The transport units 31 to 34 are connected to each other in the horizontal direction so as to transfer sample racks L. The right end of the transport unit 31 is connected to the output unit 23 so as to transfer sample racks L. The transport units 31 to 33 are disposed in front of the three measuring units 41, respectively, as shown in the drawing, and the transport unit 34 is disposed in front of the smear preparation apparatus 5 as shown in the drawing.

As shown in the drawing, in the transport units 31 to 33, two transport lines are set for a case in which a sample rack L is transported to the corresponding measuring unit 41 and for a case in which the sample rack L is not transported. That is, when measurement is performed in the measuring unit 41, the sample rack L is transported along a "measurement line" shown by the rear U-shaped arrow. When measurement is not performed in the measuring unit 41 and measurement or preparation of a smear is performed on the downstream side (left side), the sample rack L is transported along a "supply line" shown by the intermediate left-pointing arrow so as to skip the above measuring unit 41. In addition, as shown in the drawing, in the transport units 31 to 33, a right-pointing transport line for transporting a sample rack L to the recovery unit 21 is set. That is, the sample rack L which is not required to be subjected to measurement or smear preparation on the downstream side (left side) is transported along the "recovery line" shown by the front right-pointing arrow and is recovered by the recovery unit 21.

As in the transport units 31 to 33, in the transport unit 34, a measurement line, a supply line, and a recovery line are also set as shown in the drawing. At a predetermined position on the measurement line of the transport unit 34, the transport unit 34 reads the sample IDs of sample containers T each associated with a holding position in the sample rack L by a barcode unit D, and detects the presence or absence of the sample container T in each holding position in this sample rack L.

Each of the three measuring units 41 takes a container T from a rack L at a predetermined position (dotted line in the drawing) on the measurement line of each of the transport units 31 to 33 which are respectively disposed in front of the measuring units, and measures a sample contained in this container T.

That is, first, the measuring unit 41 sets the sample container T taken from the sample rack L in a sample container setting section 411a (see FIG. 8A) in the apparatus and moves the sample container T to the inside of the measuring unit 41. Next, the measuring unit 41 reads the sample ID of this sample container T by a barcode unit C in the apparatus, and detects the presence or absence of the sample container T in the sample container setting section 411a. Then, the measuring unit 41 measures the sample which is contained in this sample container T. When the measurement is completed in the measuring unit 41, the measuring unit 41 returns this sample container T to the original holding position in the sample rack L again.

The information processing unit 42 is connected to the three measuring units 41 so as to communicate therewith and controls the operations of the three measuring units 41. In addition, the information processing unit 42 is connected to the host computer 7 via a communication network so as to communicate therewith and inquires of the host computer 7 for measurement orders when the barcode unit C reads the sample ID. Then, the information processing unit 42 controls the measurement operation of the measuring unit 41 on the basis of a measurement order received from the host computer 7. In addition, the information processing unit 42 performs analysis on the basis of the result of the measurement performed by the measuring unit 41.

The smear preparation apparatus 5 suctions a sample which is contained in a sample container T at a predetermined position (dotted line arrow in the drawing) on the measurement line of the transport unit 34 disposed at the front and prepares a smear of this sample. Whether or not a smear is prepared is determined by the transport controller 6 on the basis of the result of the analysis performed by the information processing unit 42. When the transport controller 6 determines that the preparation of a smear is needed, a sample rack L containing a target sample is transported along the measurement line of the transport unit 34 and a smear is prepared in the smear preparation apparatus 5.

The transport controller 6 is connected to the recovery unit 21, the feeding unit 22, the output unit 23 and the transport units 31 to 34 so as to communicate therewith and controls the operations of the units. In addition, the transport controller 6 is connected to the host computer 7 via a communication network so as to communicate therewith. The transport controller 6 inquires of the host computer 7 for measurement orders when receiving the rack ID from the output unit 23. Then, the transport controller 6 determines a transport destination of the sample rack L output from the output unit 23 on the basis of the measurement order received from the host computer 7 and controls the devices (units) so as to transport the sample rack L to the transport destination.

Figure 3:
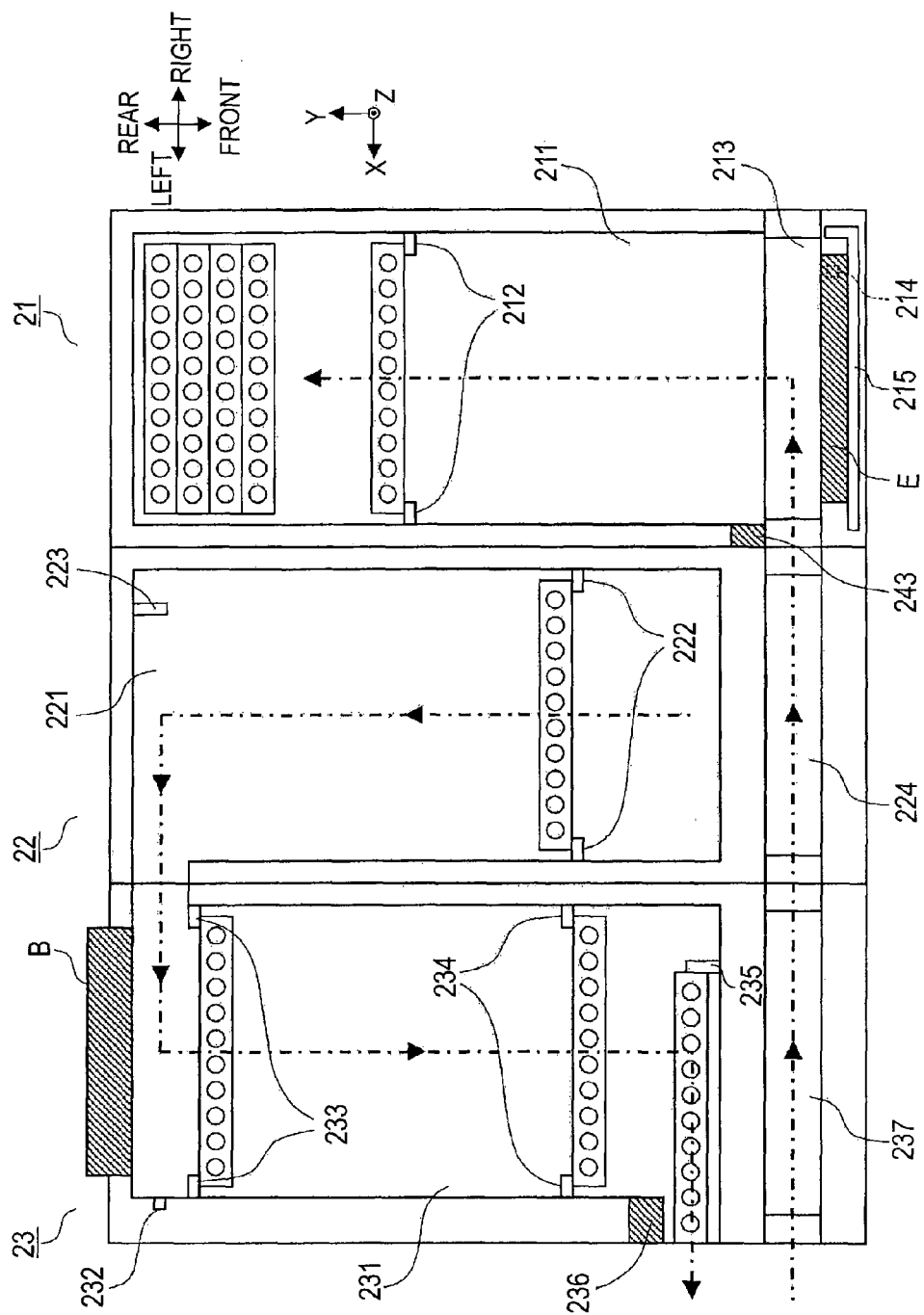
FIG. 3 is a plan view showing the configuration when a recovery unit, a feeding unit, and an output unit according to the embodiment are viewed from the upper side.

FIG. 3 is a plan view showing the configuration when the recovery unit 21, the feeding unit 22, and the output unit 23 are viewed from the upper side.

When a sample rack L is fed onto a transport passage 221 of the feeding unit 22, a rack input mechanism 222 moves backward while engaging with the front ends of the sample rack L and this sample rack L is sent to the rear position of the transport passage 221. The right side surface of the sample rack L positioned at the rear position of the transport passage 221 is pressed by a rack output mechanism 223 and is thus output to the rear position of a transport passage 231 of the output unit 23.

As shown in the drawing, a reflection type sensor 232 is disposed in the vicinity of the rear position of the transport passage 231 of the output unit 23. When the sensor 232 detects that the sample rack L output from the feeding unit 22 is positioned at the rear position of the transport passage 231, the barcode unit B reads the rack ID and the sample IDs each associated with a holding position in the sample rack L, and detects the presence or absence of the sample container T in each holding position in this sample rack L. The configuration of the barcode unit B will be explained in detail with reference to FIG. 5.

Next, by a rack input mechanism 233, the sample rack L which has been subjected to the reading and detection by the barcode unit B is sent to a position moving forward by the width in the front-back direction of the sample rack L from the rear position of the transport passage 231. Next, a rack input mechanism 234 moves forward while engaging with the rear side surface of the sample rack L and this sample rack L is sent to the front position of the transport passage 231. The right side surface of the sample rack L positioned at the front position of the transport passage 231 is pressed by a rack output mechanism 235, and thus the sample rack L is moved in the leftward direction.

In this case, when the sample rack L is slightly moved to the left from the front position of the transport passage 231 and thus the barcode label BL2 of the sample rack L is positioned in front of a barcode reader 236, the rack ID is read by the barcode reader 236. When the barcode reader 236 reads the rack ID, the output unit 23 transmits a discharge request in addition to this rack ID to the transport controller 6. On the basis of the received rack ID, the transport controller 6 determines either the measuring unit 41 or the smear preparation apparatus 5 to be a transport destination of this sample rack L.

Then, this sample rack L is further pushed in the leftward direction by the rack output mechanism 235 and output to the transport unit 31.

Next, the sample rack L which is output to the output unit 23 along the recovery line from the measuring unit 41 or the smear preparation apparatus 5 is positioned at the front position (right end position of a belt 213) of the recovery unit 21 by a belt 237 of the output unit 23, a belt 224 of the feeding unit 22, and the belt 213 of the recovery unit 21.

As shown in the drawing, a reflection type sensor 214 is disposed in the vicinity of the front position of the recovery unit 21. When the sensor 214 detects that the sample rack L is positioned at the front position of the recovery unit 21, the container detection unit E detects the presence or absence of the sample container T in each holding position in this sample rack L. In addition, the barcode reader 243 reads the rack ID of the sample rack L when the sample rack L is positioned at the front position of the recovery unit 21. The configuration of the container detection unit E will be explained in detail with reference to FIGS. 6A and 6B.

Next, the sample rack L which has been subjected to the detection by the container detection unit E is pushed onto a transport passage 211 from the front position of the recovery unit 21 by a rack pushing mechanism 215. Then, a rack input mechanism 212 moves backward while engaging with the front side surface of the sample rack L and this sample rack L is sent to the rear position of the transport passage 211. In this manner, the sample rack L holding the sample containers T which have been subjected to the measurement is gradually recovered backward on the transport passage 211 of the recovery unit 21.

FIGS. 4A to 4E are views explaining the operations of the barcode units B, C and D and the container detection unit E. FIGS. 4A to 4E are plan views schematically showing the configuration when each unit is viewed from the upper side.

FIG. 4A is a view showing the barcode unit B. As shown in the drawing, the barcode unit B includes two reading sections B1 and B2 which are juxtaposed laterally (X-axis direction). Each of the reading sections B1 and B2 includes two rollers B11, a roller B21, a base B30, and a barcode reader B31.

In the reading sections B1 and B2, the two rollers B11 are configured to rotate around the Z axis and are configured to be movable in the Y-axis direction on the base B30. The roller B21 is configured to be rotated and driven around the Z axis and is fixed onto the base B30. The barcode reader B31 is fixed to the base B30 and reads a barcode which is positioned ahead thereof (Y-axis negative direction). The base B30 is configured to be movable in the horizontal direction at the rear position of the output unit 23.

When the barcode reader B31 is positioned in front of a target holding position (in the Y-axis positive direction) in the sample rack L, first, the two rollers B11 are moved forward (Y-axis negative direction) so as to come into contact with a side surface of the sample container T. Further the front side surface (Y-axis negative direction) of the sample container T comes into contact with the roller B21.

At this time, when it is detected that the sample container T is held as described later, the roller B21 is rotated and driven, and thus the sample container T is rotated around the Z axis and the barcode reader B31 reads the barcode label BL1 during the rotation of the sample container T. On the other hand, when it is detected that the sample container T is not held as described later, the roller B21 returns in the Y-axis positive direction, and the reading at this holding position by the barcode reader B31 is not performed. When the barcode reader B31 reads the barcode label BL2 (see FIG. 2B) which is adhered between the holding positions 1 and 2 in the sample rack L, the rollers B11 are not moved forward.

The rack ID and the sample IDs at the holding positions 1 to 5 are read and the presence or absence of the sample container T is detected by a barcode reader 31 of the reading section B1. The sample IDs at the holding positions 6 to 10 are read and the presence or absence of the sample container T is detected by a barcode reader 31 of the reading section B2. At this time, the barcode readers 31 of the reading sections B1 and B2 read the barcodes in order from the left and detect the presence or absence of the sample containers T as the reading sections B1 and B2 are moved in the rightward direction (X-axis negative direction).

FIG. 4C is a view showing the barcode unit C. The barcode unit C includes two rollers C11, a roller C21, a base C30, and a barcode reader C31 as shown in the drawing. The base C30 and the barcode reader C31 are fixed to the inside of the measuring unit 41.

At a predetermined position on the measurement line of the transport unit which is disposed in front of the measuring unit 41, the sample container T, which is taken from the sample rack L, is positioned in front of the barcode reader C31 (X-axis negative direction) by the sample container setting section 411a. Next, the barcode reader C31 reads the sample IDS and detects the presence or absence of the sample container T in the front direction (X-axis negative direction) in the same order as shown in FIGS. 4A and 4B.

FIG. 4D is a view showing the barcode unit D. The barcode unit D includes two rollers D11, a roller D21, a base D30, and a barcode reader D31 as shown in the drawing. The base D30 and the barcode reader D31 are fixed in the vicinity of the measurement line of the transport unit 34. Further in this case, the barcode reader D31 reads the sample IDs and detects the presence or absence of the sample container T in the front direction (Y-axis positive direction) as in the case of the barcode unit C.

FIG. 4E is a view showing the container detection unit E. As shown in the drawing, the container detection unit E includes a sensor E11, a contacting section E13, and a base E20. The sensor E11 is configured to detect that the contacting section E13 comes into contact with the cap section CP of the sample container T. The contacting section E13 is configured to be movable with respect to the base E20 in the Z-axis direction. The base E20 is configured to be movable in the horizontal direction (X-axis direction) in front of the recovery unit 21.

When the container detection unit E detects the presence or absence of the sample container T in each holding position in the sample rack L, first, the base E20 is moved in the horizontal direction such that the contacting section E13 is positioned immediately above the target holding position (Z-axis positive direction). Next, the contacting section E13 is moved downward (Z-axis negative direction). When the sample container T is held in this holding position, the sensor E11 detects that the contacting section E13 comes into contact with the cap section CP of the sample container T, and it is recognized that the sample container T is held in this holding position. On the other hand, when the sample container T is not held in this holding position, the contacting section E13 moves in the downward direction without coming into contact with the cap section CP, and the sensor E11 does not detect that the contacting section E13 comes into contact with the cap section CP of the sample container T. Accordingly, it is recognized that the sample container T is not held in this holding position.

FIGS. 5A to 5C are views showing the configuration of the barcode unit B in detail. Since the barcode units C and D have almost the same configuration as that of the barcode unit B, a description thereof will be omitted herein.

FIG. 5A is a plan view when the vicinity of the rollers B11 and the roller B21 is viewed from the upper side. FIG. 5B is a side view when the barcode unit B is viewed from the left side (in the X-axis negative direction). FIG. 5C is a side view when the vicinity of support sections B33 and B34 is viewed from the front (in the Y-axis positive direction).

Referring to FIGS. 5A and 5B, a support body B10 is mounted with the two rollers B11, a shaft B15, and a light-shielding plate B18. In addition, the support body B10 is supported so as to be movable in the Z-axis direction by a guide (not shown) which is installed in the base B30 and extends in the Y-axis direction. In the base B30, pulleys B13a and B13b, a stepping motor B14, the barcode reader B31, and a sensor stand B39 supporting a transmission type sensor B38 including a light-emitting section and a light-receiving section are installed. The sensor stand B39 is installed so as to protrude in the X-axis positive direction from the side surface parallel to the Y-Z plane of the base B30.

The two rollers B11 are supported by the support body B10 so as to be rotatable around the Z axis. A belt B12 runs on the pulleys B13a and B13b. The pulley B13a is installed in the shaft of the stepping motor B14 so as to be rotatable around the Z axis and the pulley B13b is installed in the base B30 so as to be rotatable around the Z axis. Due to the driving of the stepping motor B14, the belt B12 moves around the pulleys B13a and B13b.

A support section B16 and a spring B17 pass through the shaft B15. The support section B16 is movable by a predetermined width in the Y-axis direction along the shaft B15. A flange section B16a is formed in the support section B16 and the flange section 16a is fixed to the belt B12. The spring B17 presses the support section B16 in the Y-axis positive direction through the extension action.

Here, when the belt B12 moves around the pulleys B13a and B13b, the support section B16 including the flange section B16a moves in the Y-axis direction. When the flange section B16a is moved in the Y-axis negative direction, the support section B16 presses the spring B17 in the Y-axis negative direction and the support body B10 moves in the Y-axis negative direction. On the other hand, when the flange section B16a is moved in the Y-axis positive direction, the support section B16 presses the side surface parallel to the X-Z plane in the Y-axis positive direction of the support body B10 in the Y-axis positive direction, and thus the support body B10 moves in the Y-axis positive direction.

In the light-shielding plate B18, light-shielding sections B18a and B18b which are planes perpendicular to the X axis are formed. The light-shielding sections B18a and B18b are configured to be positioned between the light-emitting section and the light-receiving section of the sensor B38 when the support body B10 is moved in the Y-axis direction. When the barcode reader B31 is positioned in front of the holding position in the target sample rack L (Y-axis positive direction), the support body B10 is moved in the Y-axis negative direction from the state in which the light-shielding section B18a is positioned between the light-emitting section and the light-receiving section of the sensor B38 as shown in FIGS. 5A and 5B.

Here, in the case where the sample container T is held in the holding position in the sample rack L positioned in front of the barcode reader B31, when the support body B10 is moved in the Y-axis negative direction, the two rollers B11 come into contact with a side surface of the sample container T. At this time, the support section B16 moves in the Y-axis negative direction while contracting the spring B17 in accordance with the movement of the belt B12, but there is no further movement of the support body B10 in the Y-axis negative direction. Accordingly, when the support section B16 moves by a predetermined width, when the light-shielding section B18b is not positioned between the light-emitting section and the light-receiving section of the sensor B38, it is recognized that the sample container T is held in this holding position.

On the other hand, when the sample container T is not held in the holding position in the sample rack L positioned in the Y-axis negative direction of the barcode reader B31, when the support body B10 moves in the Y-axis negative direction by a predetermined width, the light-shielding section B18b is positioned between the light-emitting section and the light-receiving section of the sensor B38. Accordingly, it is recognized that the sample container T is not held in this holding position.

In this manner, when a mechanism for driving the support body B10 is configured, when the support body B10 is moved in the Y-axis direction, the presence or absence of the sample container T in the holding position in the sample rack L positioned in front of the barcode reader B31 is detected by the output signal of the sensor B38 and the movement width of the support section B16 which is obtained from the stepping motor B14. In addition, when it is detected that the sample container T is held, the barcode reader B31 reads the sample ID of the sample container T.

Referring to FIG. 5B, a support body B20 is mounted with a roller B21, a shaft B22, and a pulley B24b. The support body B20 is screwed to the base B30.

The roller B21 has a hole formed therethrough in the Z-axis direction. The shaft B22 passes through this hole and supports the roller B21. In addition, both ends of the shaft B22 are supported by the support member B20 so as to be rotatable around the Z axis. A belt B23 runs on the pulleys B24a and B24b. The pulley B24a is installed in the shaft of a stepping motor B25 so as to be rotatable around the Z axis and the pulley B24b is installed in the support member B20 and the support shaft B22 so as to be rotatable around the Z axis. The stepping motor B25 is installed in the base B30.

In this manner, when a mechanism for driving the roller B21 is configured, the belt B23 moves around the pulleys B24a and B24b due to the driving of the stepping motor B25. Accordingly, the shaft B22 and the roller B21 are rotated around the Z axis.

Referring to FIGS. 5B and 5C, the barcode reader B31, a receiving section B32, two belts B35, two pulleys B36a, two pulleys B36b, and two stepping motors B37 are disposed on the lower surface (surface in the Z-axis negative direction) of the base B30.

The barcode reader B31 and the receiving section B32 are installed on the lower surface of the base B30. The support sections B33 and B34 are installed on the lower surfaces of the bases B30 of the reading sections B1 and B2 (see FIG. 4A), respectively. A guide 23b extending in the X-axis direction is installed on the upper surface of a support section 23a which is installed at the back (end in the Y-axis positive direction) of the output unit 23. The base B30 is supported so as to be movable in the X-axis direction on the guide 23b via the receiving section B32.

The two pulleys B36a and the two pulleys B36b are installed on the side surface in the Y-axis positive direction of the support section 23a of the output unit 23 so as to be rotatable around the Y axis. As shown in the drawing, the two belts B35 run on the pulleys B36a and B36b. The support sections B33 and B34 are fixed to the upper and lower belts B35, respectively. The two stepping motors B37 are installed in the support section 23a and are connected to the two pulleys B36a.

In this manner, when a mechanism for driving the base B30 is configured, the two belts B35 move around the pulleys B36a and B36b due to the driving of the two stepping motors B37. Accordingly, the support sections B33 and B34 are moved in the X-axis direction and thus the bases B30 of the reading sections B1 and B2 are moved individually in the X-axis direction.

FIGS. 6A and 6B are views showing the configuration of the container detection unit E in detail.

FIG. 6A is a side view when the container detection unit E is viewed from the right side (in the X-axis positive direction). FIG. 6B is a plan view when the container detection unit E is viewed from the upper side. Although a mechanism for moving the base E20 in the X-axis direction is configured in the downward direction (Z-axis negative direction) of the container detection unit E, such a mechanism is the same as the barcode unit B shown in FIGS. 5A to 5C, and thus it will not be shown in the drawing.

Referring to FIGS. 6A and 6B, a support body E10 is mounted with the transmission type sensor E11 including a light-emitting section and a light-receiving section, a light-shielding plate E12, the contacting section E13, a receiving section E14, an upper plate section E15, and a shaft E16. Pulleys E22a and E22b, a stepping motor E23, transmission type sensors E24 and E25 including a light-emitting section and a light-receiving section, and a guide E26 are installed in the base E20.

The sensor E11 detects whether or not a light-shielding plate E19 to be described later is positioned between the light-emitting section and the light-receiving section of the sensor E11. The light-shielding plate E12 is positioned between a light-emitting section and a light receiving section of the sensor E24 and between a light-emitting section and a light-receiving section of the sensor E25 when the support body E10 moves in the Z-axis direction. The contacting section E13 is installed on the lower surface (surface in the Z-axis negative direction) of the end in the Y-axis positive direction of the support body E10. When there is a sample container T immediately below the contacting section E13 (Z-axis negative direction), the contacting section E13 comes into contact with a cap section CP of the sample container T from the state of FIG. 6A when the support body E10 is moved in the Z-axis negative direction. The receiving section E14 is installed in the guide E26 and is movable in the Z-axis direction along the guide E26. Accordingly, the support body E10 is movable in the Z-axis direction via the receiving section E14.

The upper plate section E15 supports the end section in the Z-axis positive direction of the shaft E16. A flange section E10a is formed in the support body E10 and the flange section E10a supports the end section in the Z-axis negative direction of the shaft E16. A support section E17 and a spring E18 pass through the shaft E16. The support section E17 is fixed to a belt E21 and is movable by a predetermined width in the Z-axis direction along the shaft E16. The spring E18 presses the support section E17 in the Z-axis positive direction through the extension action. The light-shielding plate E19 is installed in the support section E17.

The belt E21 runs on the pulleys E22a and E22b. The pulley E22a is installed in the shaft of the stepping motor E23 so as to be rotatable around the Y axis and the pulley E22b is installed in the base E20 so as to be rotatable around the Z axis. Due to the driving of the stepping motor E23, the belt E21 moves around the pulleys E22a and E22b.

Here, when the belt E21 moves around the pulleys E22a and E22b, the support section E17 moves in the Z-axis direction. When the support section E17 moves in the Z-axis negative direction, the support body E10 receives the force from the spring E18 and moves in the Z-axis negative direction. In addition, when the support section E17 moves in the Z-axis positive direction, the support section E17 presses the upper plate section E15 in the Z-axis positive direction and thus the support body E10 moves in the Z-axis positive direction.

In a case where a sample container T is positioned immediately below the contacting section E13 (Z-axis negative direction), when the support body E10 is moved in the Z-axis negative direction from the state in which the light-shielding plate E12 is positioned at the sensor E24, the light-shielding plate E19 is positioned between a light-emitting section and a light-receiving section of the sensor E11. That is, when the contacting section E13 comes into contact with the upper surface of the cap section CP of the sample container T, there is no further movement of the support body E10 in the downward direction, but the support section E17 moves in the downward direction (Z-axis negative direction) while contracting the spring E18 in accordance with the movement of the belt E21. Accordingly, since the light-shielding plate E19 is positioned between the light-emitting section and the light-receiving section of the sensor E11, it is recognized that the sample container T is positioned immediately below the contacting section E13.

On the other hand, in the case where the sample container T is not positioned immediately below the contacting section E13 (Z-axis negative direction), even when the support body E10 is moved in the Z-axis negative direction from the state in which the light-shielding plate E12 is positioned at the sensor E24, the light-shielding plate E19 is not positioned between the light-emitting section and the light-shielding section of the sensor E11, and the light-shielding plate E12 is positioned at the sensor E25. Accordingly, it is recognized that the sample container T is not positioned immediately below the contacting section E13.

In this manner, when a mechanism for driving the support body E10 is configured, when the support body E10 is moved in the downward direction (Z-axis negative direction), the presence or absence of the sample container T in the holding position in the sample rack L positioned below the contacting section E13 is detected by the output signal of the sensor E11.

Figure 7:
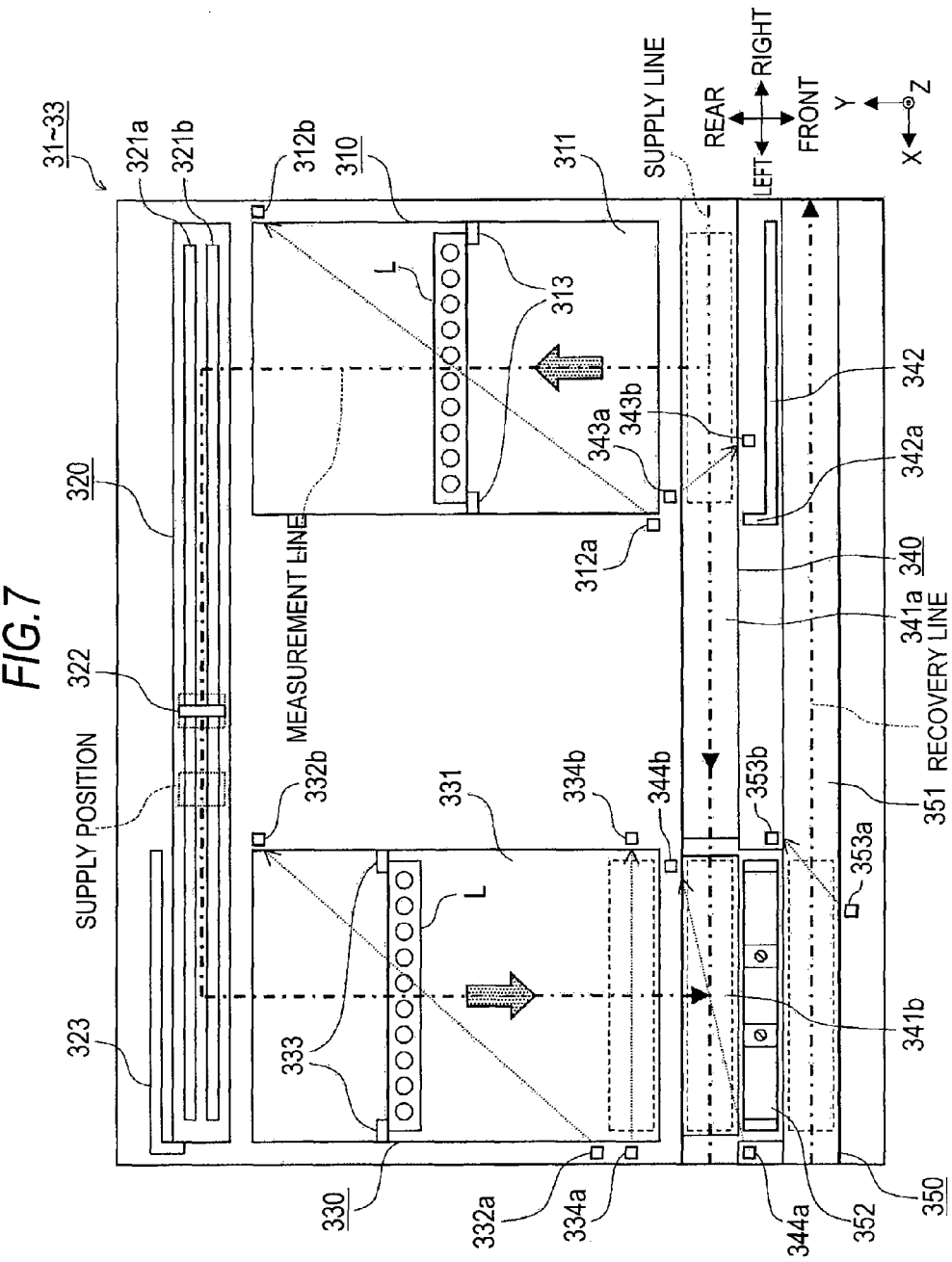
FIG. 7 is a plan view showing the configuration when a transport unit according to the embodiment is viewed from the upper side.

FIG. 7 is a plan view showing the configuration when the transport units 31 to 33 are viewed from the upper side. The transport units 31 to 33 include a right table 310, a rack transport section 320, a left table 330, and rack transport sections 340 and 350. The right table 310, the rack transport section 320, and the left table 330 constitute the measurement line in FIG. 1. In addition, the rack transport section 340 constitutes the supply line in FIG. 1, and the rack transport section 350 constitutes the recovery line in FIG. 1. The transport units 31 to 33 have the same configuration.

When the measurement of the sample rack L output from the upstream side (right side) is not performed by the measuring unit 41 corresponding to this transport unit, this sample rack L is linearly sent along the supply line to the left end from the right end of the rack transport section 340 by belts 341a and 341b of the rack transport section 340. Transmission type sensors 344a and 344b are installed in the vicinity of the left end of the rack transport section 340. The sample rack L which is positioned at the left end position of the rack transport section 340 is detected by the sensors 344a and 344b.

Next, when the measurement of the sample rack L output from the upstream side (right side) is performed by the measuring unit 41 corresponding to this transport unit, this sample rack L is positioned at the right end position of the rack transport section 340. That is, a rack pushing mechanism 342 is moved backward such that a wall section 342a slightly appears on the supply line from the state shown in the drawing. Accordingly, the sample rack L output from the upstream side hits the wall section 342a and is thus stopped. In addition, transmission type sensors 343a and 343b are installed in the vicinity of the right end position of the rack transport section 340. The sample rack L which is positioned at the right end position of the rack transport section 340 is detected by the sensors 343a and 343b.

Next, due to the further backward movement of the rack pushing mechanism 342, this sample rack L is pushed to the front end of a transport passage 311 of the right table 310. When the sample rack L on the transport passage 311 is detected by transmission type sensors 312a and 312b, a rack input mechanism 313 moves backward while engaging with the front ends of the sample rack L and the sample rack L is sent backward. When the sample rack L is sent up to the right end position of the rack transport section 320, belts 321a and 321b are driven and the sample rack L is sent in the leftward direction. Since the belts 321a and 321b are driven by a stepping motor (not shown), the sample rack L on the rack transport section 320 is transported with high accuracy for each step number of the stepping motor.

Thereafter, the sample rack L reaches the position of a container sensor 322. The container sensor 322 is a contact type sensor. When the sample container T which is held in the sample rack L passes a position immediately below the container sensor 322, the contact piece of the container sensor 322 is bent by the sample container T and the presence of the sample container T is detected.

At a supply position positioned on the left side of the position at which the sample container T is detected by the container sensor 322, by a distance corresponding to two sample containers T, hand sections F15a and F15b (see FIG. 8A) of the measuring unit 41 grip the sample container T and take out the sample container T from the sample rack L. The removed sample container T returns again to the sample rack L after being used in the measurement in the measuring unit 41. The transport of the sample rack L is put on hold during the period until the sample container T returns to the sample rack L.

In this manner, when the processing of all the sample containers T, which are to be processed by the measuring unit 41 corresponding to this transport unit, among the sample containers T held in the sample rack L ends, the sample rack L is sent up to the left end position of the rack transport section 320 by the belts 321a and 321b. Thereafter, the sample rack L is pushed to the rear end of a transport passage 331 of the left table 330 by a rack pushing mechanism 323. When the sample rack L on the transport passage 331 is detected by transmission type sensors 332a and 332b, a rack input mechanism 333 moves forward while engaging with the rear ends of the sample rack L. Accordingly, the sample rack L is sent forward.

Transmission type sensors 334a and 334b are installed in the vicinity of the forward part of the left table 330. The sample rack L positioned at the front position of the left table 330 is detected by the sensors 334a and 334b.

Next, at the front of the left table 330, a partition section 352 between the rack transport sections 340 and 350 is controlled so as to be opened or closed and the sample rack L is positioned in either the rack transport section 340 or in the rack transport section 350.

When it is necessary to perform processing such as the measurement in the measuring unit 41 on the downstream side or in the smear preparation apparatus 5 on any of the sample containers T held in the sample rack L, the sample rack L is moved up to the left end position of the rack transport section 340 by the rack input mechanism 333 in the state in which the rack transport sections 340 and 350 are partitioned by the partition section 352. Then, this sample rack L is output to the transport unit on the downstream side by the belt 341b of the rack transport section 340.

On the other hand, when it is not necessary to perform processing such as the measurement in the measuring unit 41 on the downstream side or in the smear preparation apparatus 5 on any sample container T held in the sample rack L, the upper surface of the partition section 352 is lowered to the same level in height as that of the upper surface of the belt 341b of the rack transport section 340 and the sample rack L is moved up to the left end position of the rack transport section 350 by the rack input mechanism 333. In this manner, the sample rack L is moved up to the left end position of the rack transport section 350 from the left table 330 across the rack transport section 340 by the rack input mechanism 333. The sample rack L positioned at the left end position of the rack transport section 350 is detected by transmission type sensors 353a and 353b installed in the vicinity of the left end position of the rack transport section 350. Then, this sample rack L is moved in the rightward direction along the recovery line by a belt 351 of the rack transport section 350. The sample rack L transported along the recovery line is accommodated in the recovery line 21.

The transport unit 34 has the barcode unit D installed in the vicinity of the right end of the rack transport section 320 in addition to the same configuration as those of the transport units 31 to 33. When the sample rack L including a sample which is judged to be required to be subjected to smear preparation is transported to the transport unit 34, this sample rack L is transported along the measurement line. At this time, the sample ID of the sample container T which is held in the sample rack L is read by the barcode unit D before the sample container T reaches the supply position. When the sample container T is positioned at the supply position, the sample is suctioned from the sample container T and smear preparation is performed in the smear preparation apparatus 5. Then, this sample rack L is transported in the rightward direction toward the recovery unit 21 along the recovery line.

Figure 8B:
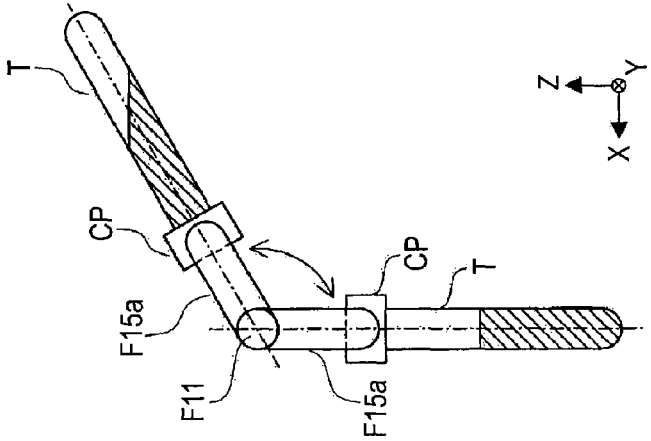
FIG. 8B is a view explaining inversion stirring of a sample container.
Figure 8A:
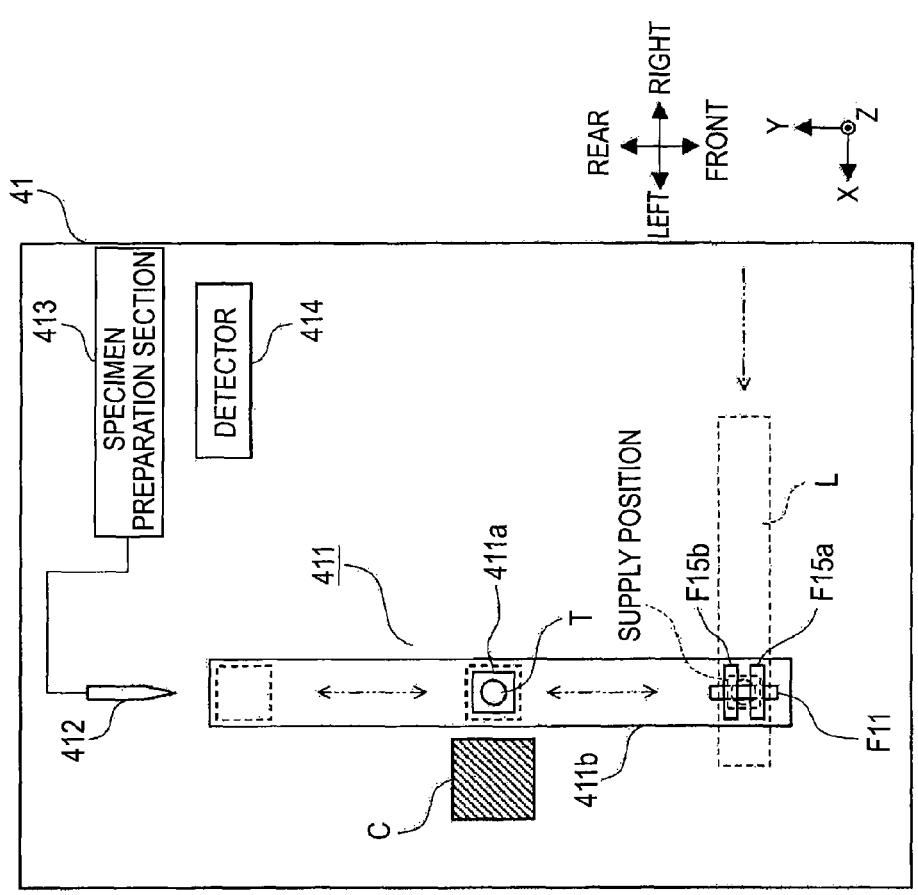
FIG. 8A is a plan view schematically showing the configuration when a measuring unit according to the embodiment is viewed from the upper side.

FIG. 8A is a plan view schematically showing the configuration when the measuring unit 41 is viewed from the upper side.

The hand sections F15a and F15b are configured such that the cap section CP of the sample container T which is positioned at the supply position is sandwiched therebetween in the Y-axis direction. In addition, the hand sections F15a and F15b pass through a rotation shaft F11 parallel to the Y axis.

A sample container transport section 411 includes a sample container setting section 411a and a transport mechanism section 411b. The sample container setting section 411a is configured to be movable in the front-back direction up to a position at which the suction by a sample suction section 412 can be performed from the supply position by the transport mechanism section 411b. The transport mechanism section 411b includes a belt (not shown), two pulleys and a stepping motor.

When the sample container T is positioned at the supply position on the measurement line, the hand sections F15a and F15b are moved in the downward direction (Z-axis negative direction) toward the sample container T positioned at the supply position. Next, the hand sections F15a and F15b grip the cap section CP of the sample container T and take the gripped sample container T in the upward direction (Z-axis positive direction) from the sample rack L. The sample container T taken from the sample rack L is subjected to inversion stirring plural times as shown in FIG. 8B due to the rotation of the rotation shaft F11 around the Y axis while being gripped by the hand sections F15a and F15b. At this time, the sample container setting section 411a is positioned immediately below the hand sections F15a and F15b.

When the inversion stirring of the sample container T ends, the hand sections F15a and F15b are moved in the downward direction (Z-axis negative direction) and the sample container T is set in the sample container setting section 411a. Next, the sample container setting section 411a is moved backward and positioned in front of the barcode unit C (X-axis negative direction). In this state, as explained with reference to FIG. 4C, the barcode unit C reads the sample ID and detects the presence or absence of the sample container T. The information read by the barcode unit C and the detected information are transmitted to the information processing unit 42.

Next, the sample container T is positioned immediately below the sample suction section 412 (Z-axis negative direction) due to the further backward movement of the sample container setting section 411a. The sample suction section 412 suctions the sample in the sample container T positioned immediately below the sample suction section 412.

Thereafter, the sample container T returns along the original route and is positioned again immediately below the hand sections F15a and F15b (Z-axis negative direction). The hand sections F15a and F15b grip and move this sample container T upward (Z-axis positive direction). At this time, the sample container setting section 411a is moved backward (Y-axis positive direction). Next, the hand sections F15a and F15b move in the downward direction (Z-axis negative direction) and the sample container T returns to the original holding position in the sample rack L.

A specimen preparation section 413 has a plurality of reaction chambers (not shown). The specimen preparation section 413 mixes and stirs a reagent and the sample suctioned by the sample suction section 412 in a reaction chamber and prepares a specimen for measurement. A detector 414 measures the specimen prepared by the specimen preparation section 413. The measurement data obtained by such measurement is analyzed by the information processing unit 42.

FIGS. 9A and 9B are views showing the configuration of a gripping unit F in detail.

FIG. 9A is a plan view when the gripping unit F is viewed from the upper side (in the Z-axis negative direction), and FIG. 9B is a side view when the gripping unit F is viewed from the right side (in the X-axis positive direction).

Referring to FIGS. 9A and 9B, a support body F10 is mounted with a rotation shaft F11, an air cylinder F12, support plates F13 and F14, hand sections F15a and F15b, a shaft F16, and a spring F17.

The support body 10 is supported by a base F20 so as to be rotatable around the rotation shaft F11. The rotation shaft F11 is fixed to flange sections F10a and F10b of the support body F10. Furthermore, one end of the rotation shaft F11 is supported by a flange section F20a of the base F20 so as to be rotatable, and the other end is fixed to the driving shaft of a stepping motor F18 mounted on the base F20. When the stepping motor F18 is driven, the support body F10 rotates around the rotation shaft F11, and the air cylinder F12, the support plates F13 and F14, the hand sections F15a and F15b, the shaft F16, and the spring F17 rotate integrally therewith.

The hand sections F15a and F15b pass through the rotation shaft F11. The hand section F15a is movable along the rotation shaft F11. The support plates F14 and F13 are fixed to the hand sections F15a and F15b, respectively. The support plate F13 is fixed to the shaft F16 mounted on the support body F10. The support plate F14 is connected to a shaft F12a protruding from the air cylinder F12. In addition, a hole of the support plate F14 passes through the shaft F16. The air cylinder F12 moves the shaft F12a in the Y-axis direction. When the air cylinder F12 is driven, the driving force thereof is transmitted to the hand section F15a via the support plate F14 and the shaft F12a, and the hand section F15a moves along the rotation shaft F11.

Both ends of the spring F17 are fixed to the support plates F13 and F14. The spring F17 presses the support plate F14 in the Y-axis negative direction through the extension action. The stepping motor F18 is installed in the base F20. As described above, an end portion in the Y-axis direction of the rotation shaft F11 is fixed to the driving shaft of the stepping motor F18.

Next, on an inner wall 41a of the measuring unit 41, pulleys F21a and F21b are installed so as to be rotatable around the Y axis. In addition, a stepping motor F23 and a guide 41b are installed on the inner wall 41a. The pulley F21a is installed on the shaft of the stepping motor F23 so as to be rotatable around the Y axis. A belt F22 runs on the pulleys F21a and F21b and the base F20 is fixed to the belt F22. A receiving section F24 is installed on the base F20. Accordingly, the base F20 is movable in the Z-axis direction along the guide 41b via the receiving section F24.

In this manner, when the gripping unit F is configured, when the shaft F12a is moved by the air cylinder F12 in the Y-axis positive direction against the spring F17 from the state shown in FIGS. 9A and 9B, the hand section F15a moves in the Y-axis positive direction along the rotation shaft F11. Accordingly, the cap section CP of the sample container T positioned between the hand sections F15a and F15b is gripped by the hand sections F15a and F15b. On the other hand, when the shaft F12a is moved by the air cylinder F12 in the Y-axis negative direction from the state in which the cap section CP is gripped by the hand sections F15a and F15b, the hand section F15a is positioned at the position in FIG. 9A and the gripped cap section CP is released.

In addition, when the stepping motor F18 is driven, the rotation shaft F11 rotates around the Y axis and the hand sections F15a and F15b are rotated around the Y axis along with the support body F10. Furthermore, when the stepping motor F23 is driven, the belt F22 moves and the base E20 moves in the Z-axis direction.

As explained with reference to FIGS. 8A and 8B, the gripping unit F takes the sample container T from the sample rack L and the sample container T is subjected to inversion stirring. In addition, the sample container T which has been subjected to inversion stirring is set in the sample container setting section 411a by the gripping unit F, and the sample container T which has been subjected to the measurement is taken from the sample container setting section 411a and returns to the original holding position in the sample rack L.

Figure 10:
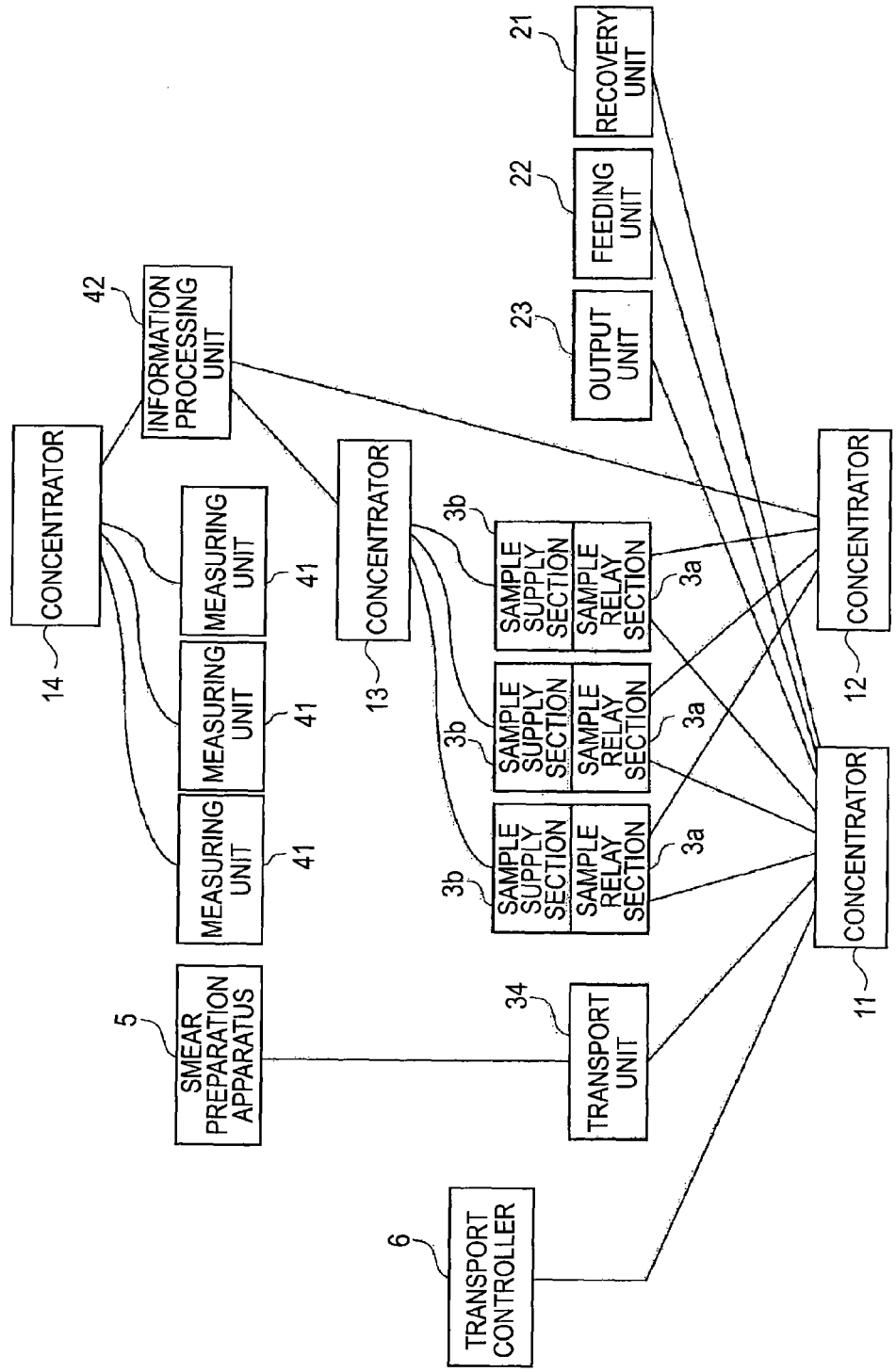
FIG. 10 is a view schematically showing the connection relationship between the units (devices) in the sample processing system according to the embodiment.

FIG. 10 is a view schematically showing the connection relationship between the units (devices) of the sample processing apparatus 1.

Here, each of the transport units 31 to 33 is divided into a sample relay section 3a and a sample supply section 3b in the drawing. In greater detail, the sample relay section 3a includes the left table 330 and the rack transport sections 340 and 350 in FIG. 7. The sample relay section 3a receives a sample rack L from one of the two neighboring transport units and transports the sample rack L to the other transport unit. The sample supply section 3b includes the right table 310 and the rack transport section 320 in FIG. 7 and transports a sample rack L to the supply position in order to measure the sample by the measuring unit 41.

The recovery unit 21, the feeding unit 22, the output unit 23, the three sample relay sections 3a, the transport unit 34, and the transport controller 6 are connected to a concentrator 11 so as to communicate therewith. The three sample relay sections 3a and the information processing unit 42 are connected to a concentrator 12 so as to communicate therewith. The three sample supply sections 3b and the information processing unit 42 are connected to a concentrator 13 so as to communicate therewith. The three measuring units 41 and the information processing unit 42 are connected to a concentrator 14 so as to communicate therewith.

Figure 11:
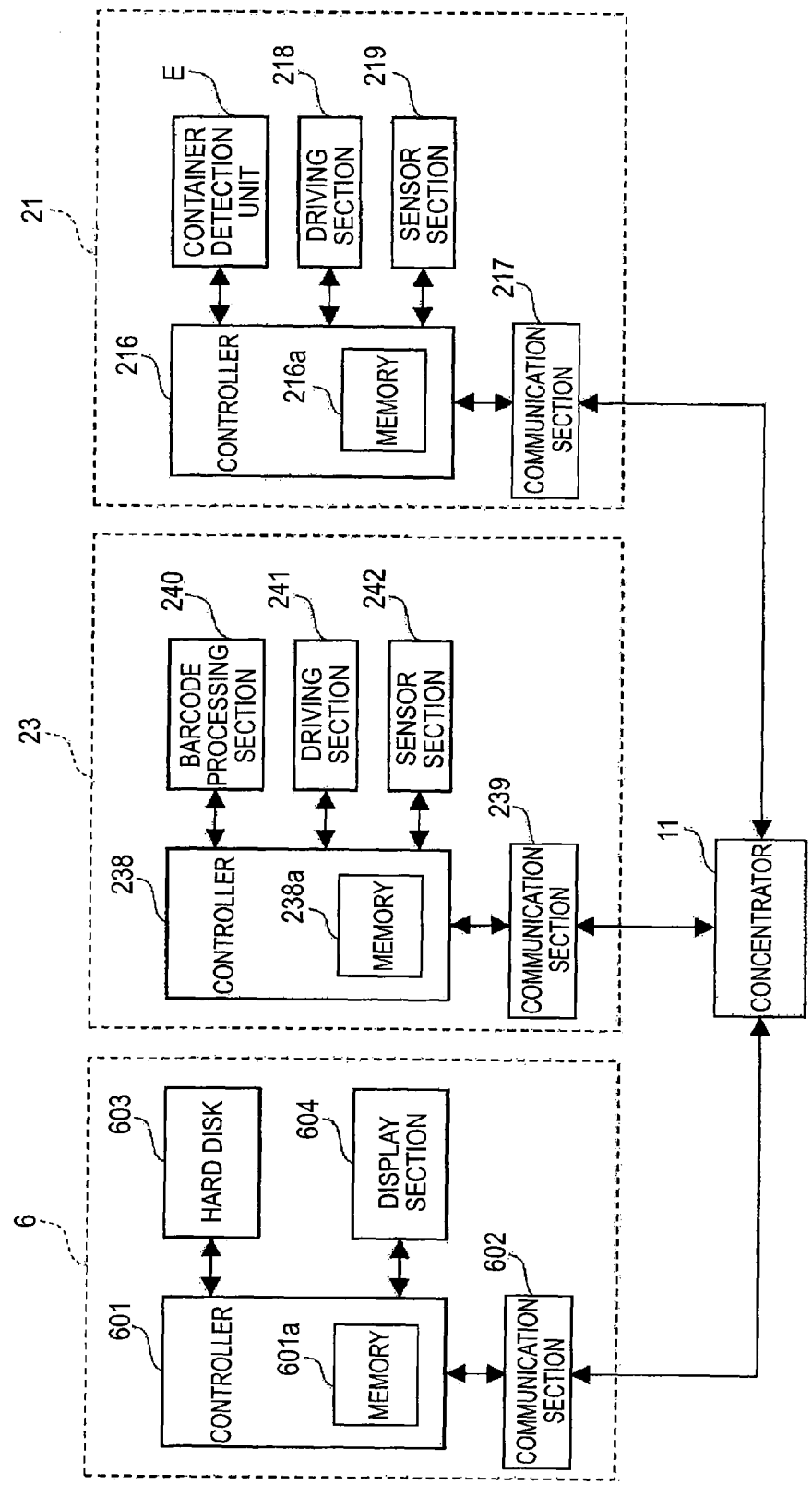
FIG. 11 is a view showing an outline of the configurations of a transport controller, the output unit, and the recovery unit according to the embodiment.

FIG. 11 is a view showing an outline of the configurations of the transport controller 6, the output unit 23, and the recovery unit 21.

The transport controller 6 includes a controller 601, a communication section 602, a hard disk 603, and a display section 604. In addition, the controller 601 includes a memory 601a.

The controller 601 controls other units (devices) by executing a computer program which is stored in the memory 601a or the hard disk 603. The memory 601a is used in the readout of computer programs stored in the hard disk 603 and is also used as a working area when these computer programs are executed. The communication section 602 includes a communication interface for performing data communication with an exterior device on the basis of Ethernet (registered trade name) standard and performs data communication with the concentrator 11.

A computer program for controlling other units (devices) is stored on the hard disk 603. In addition, a computer program for displaying on the display section 604 a loss notification screen of a sample container T, a progress screen, and a recovery state screen of a sample container T, which will be described later, is stored on the hard disk 603. The display section 604 is formed of a display or the like and displays an image on the basis of a video signal output from the controller 601.

The output unit 23 includes a controller 238, a communication section 239, a barcode processing section 240, a driving section 241, and a sensor section 242. In addition, the controller 238 includes a memory 238a.

The controller 238 controls the sections in the output unit 23 by executing a computer program stored on the memory 238a in the controller 238 in accordance with the controller 601 of the transport controller 6. The communication section 239 performs data communication with the concentrator 11 as in the case of the communication section 602 of the transport controller 6.

The barcode processing section 240 includes the barcode unit B and the barcode reader 236 shown in FIG. 3. The barcode information read by the barcode unit B and the barcode reader 236 is output to the controller 238. In addition, output is also performed in regards to the presence or absence of the sample container T detected by the barcode unit B to the controller 238. The controller 238 stores the information received from the barcode processing section 240 on the memory 238a and transmits the information to the transport controller 6 via the communication section 239 and the concentrator 11.

The driving section 241 includes a mechanism for transporting a sample rack L on the output unit 23 and a stepping motor for driving this mechanism. The sensor section 242 includes a sensor for detecting a sample rack L on the output unit 23 other than the sensor 232. The sensor section 242 outputs a detection signal to the controller 238.

As shown in the drawing, the recovery unit 21 has a configuration in which the container detection unit E is added in place of the barcode processing section 240 of the output unit 23.

A controller 216 controls the sections in the output unit 23 by executing a computer program which is stored on a memory 216a in the controller 216 in accordance with the controller 601 of the transport controller 6. A communication section 217 performs data communication with the concentrator 11 as in the case of the communication section 239 of the output unit 23.

The presence or absence of the sample container T detected by the container detection unit E is output to the controller 216. The controller 216 stores the information received from the container detection unit E on the memory 216a and transmits the information to the transport controller 6 via the communication section 217 and the concentrator 11.

The driving section 218 includes a mechanism for transporting a sample rack L on the recovery unit 21 and a stepping motor for driving this mechanism. The sensor section 219 includes a sensor for detecting a sample rack L on the recovery unit 21 in addition to the sensor 214. The sensor section 219 outputs a detection signal to the controller 216.

The feeding unit 22 has the same configuration as the configuration in which the barcode processing section 240 is omitted from the output unit 23 and this will be omitted in the drawing.

Figure 12:
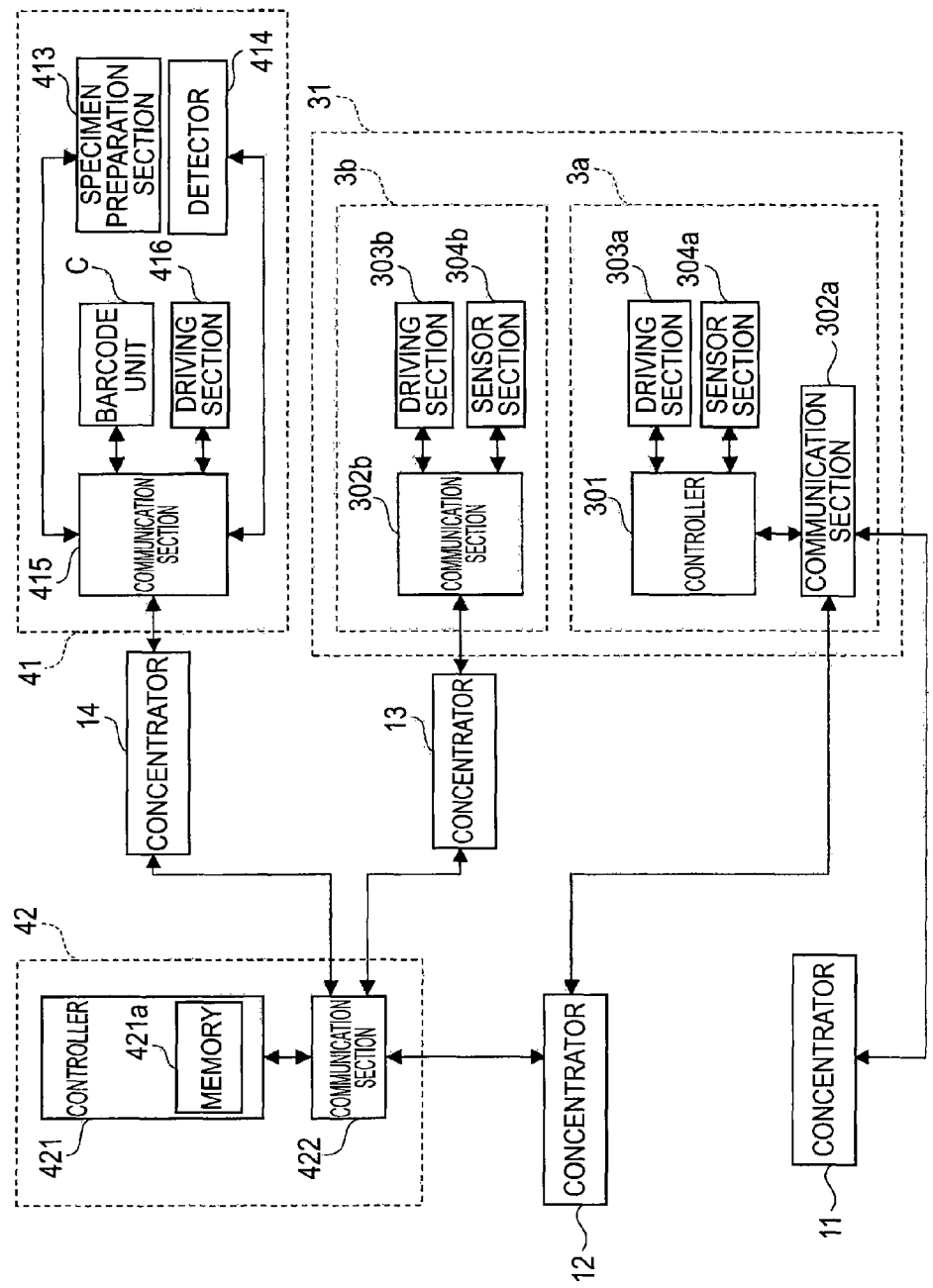
FIG. 12 is a view showing an outline of the configurations of the transport unit, the measuring unit, and an information processing unit according to the embodiment.

FIG. 12 is a view showing an outline of the configurations of the transport unit 31, the measuring unit 41, and the information processing unit 42. In the same drawing, for the sake of convenience, only one transport unit 31 and only one measuring unit 41 are shown. However, the transport units 32 and 33 and the other measuring units 41 also have the same configuration.

The transport unit 31 has a configuration (memory is not shown) in which the barcode processing section 240 is omitted from the output unit 23 in FIG. 11, and a communication section 302b, a driving section 303b, and a sensor section 304b are added.

A communication section 302a performs data communication with the concentrators 11 and 12 and the communication section 302b performs data communication with the concentrator 13 as in the case of the communication section 302a. A driving section 303a is controlled by a controller 301 and the driving section 303b is controlled by the information processing unit 42 via the communication sections 302b. A sensor section 304a outputs a detection signal to the controller 301 and the sensor section 304b outputs a detection signal to the information processing unit 42 via the communication section 302b.

The communication section 302b, the driving section 303b, and the sensor section 304b are included in the sample supply section 3b in FIG. 10. The sections other than the communication section 302b, the driving section 303b, and the sensor section 304b in the transport unit 31 are included in the sample relay section 3a in FIG. 10. The driving section 303a and the sensor section 304a include a mechanism for transporting and detecting sample racks L on the left table 330 and the rack transport sections 340 and 350 in FIG. 7. The driving section 303b and the sensor section 304b include a mechanism for transporting and detecting sample racks L on the right table 310 and the rack transport section 320 in FIG. 7.

The measuring unit 41 includes a communication section 415 and a driving section 416 in addition to the barcode unit C, the specimen preparation section 413, and the detector 414 shown in FIG. 8.

The communication section 415 performs data communication with the concentrator 14 as in the case of the communication section 302b of the transport unit 31.

The driving section 416 includes the gripping unit F shown in FIGS. 9A and 9B, the sample container transport section 411 for transporting a sample container T shown in FIG. 8A, the sample suction section 412, and a mechanism for driving these.

The information processing unit 42 has the same configuration (hard disk and display section are not shown) as that of the transport controller 6 in FIG. 11.

A controller 421 controls the driving section 303b of the transport unit 31 via a communication section 422 and the concentrator 13 and receives a detection signal of the sensor section 304b. In addition, the controller 421 controls the driving section 416 of the measuring unit 41 via the communication section 422 and the concentrator 14, and receives the sample ID read by the barcode unit C and the detected presence or absence of the sample container T. The controller 421 stores the information received from the barcode unit C on a memory 421a and transmits the information to the transport controller 6 via the communication sections 422 and 302a, and the concentrators 11 and 12.

FIG. 13 is a view showing an outline of the configurations of the transport unit 34 and the smear preparation apparatus 5.

The transport unit 34 has a configuration in which the barcode unit D is added in place of the barcode processing section 240 from the output unit 23 in FIG. 11.

A communication section 342 performs data communication with the concentrator 11. In addition, the communication section 342 is connected to a communication section 502 of the smear preparation apparatus 5 by a signal line and also performs data communication with the communication section 502. A controller 341 receives the sample ID read by the barcode unit D and the detected presence or absence of the sample container T. The controller 341 stores the information received from the barcode unit D on a memory 341a and transmits the information to the transport controller 6 via the communication section 342 and the concentrator 11.

The smear preparation apparatus 5 has the same configuration (memory is not shown) as the configuration in which the barcode processing section 240 is omitted from the output unit 23 in FIG. 11.

A controller 501 of the smear preparation apparatus 5 suctions a sample from a sample container T disposed at the supply position on the measurement line of the transport unit 34 and prepares a smear when receiving a smear preparation instruction from the transport unit 34 via the communication section 502.

FIG. 14A is a flowchart showing a process of the transport controller 6 in the reading operation of the barcode unit B.

The controller 601 of the transport controller 6 puts the process on hold until a sample rack L reaches the rear position of the transport passage 231 of the output unit 23 (S11). That is, the controller 601 puts the process on hold until receiving the fact that the sample rack L has been detected by the sensor 232 from the output unit 23.

When the sample rack L reaches the rear position of the transport passage 231 of the output unit 23 (S11: YES), the controller 601 instructs the output unit 23 to perform a reading operation by the barcode unit B (S12). When receiving the reading operation instruction, the output unit 23 drives the barcode unit B to read the rack ID and the sample IDs associated with the holding positions in the sample rack L and to detect the presence or absence of the sample container T in each holding position in this sample rack L as described above.

FIG. 14B is a view conceptually showing an example of the information which is obtained by the reading operation of the barcode unit B, that is, the rack ID, the sample IDs associated with the holding positions in the sample rack L, and the presence or absence of the sample container T in each holding position in this sample rack L. Hereinafter, the information which is obtained by the reading operation of the barcode unit B is referred to as "rack information".

As shown in the drawing, according to the rack information in this case, it is recognized that no sample container T is held in the holding positions 4 and 5 in the sample rack L. When obtaining the rack information by the reading operation of the barcode unit B, the output unit 23 transmits this rack information to the transport controller 6.

Returning to FIG. 14A, the controller 601 of the transport controller 6 puts the process on hold until receiving the rack information from the output unit 23 (S13). When receiving the rack information from the output unit 23 (S13: YES), the controller 601 stores this rack information on the hard disk 603 (S14). In addition, the controller 601 stores the date and time at which this rack information is received on the hard disk 603. Next, the controller 601 inquires of the host computer 7 for measurement orders on the basis of the sample IDs included in the rack information and obtains the measurement orders from the host computer 7 (S15).

In this manner, the process of FIG. 14A is repeated for each sample rack L which reaches the rear position of the output unit 23 in the transport controller 6.

FIGS. 15A and 15B are flowcharts showing processes of the output unit 23 in the reading operation of the barcode unit B. In S12 of FIG. 14A, when receiving the instruction to perform the reading operation by the barcode unit B from the transport controller 6, the controller 238 of the output unit 23 executes the two processes shown in FIGS. 15A and 15B in parallel.

Referring to FIG. 15A, the controller 238 generates a variable i in the memory 238a in the controller 238 and sets this variable i to 1 (S101). When the value of the variable i is 2 (S102: YES), the controller 238 positions the reading section B1 of the barcode unit B in front of the barcode label BL2 of the sample rack L which is at the rear position of the output unit 23 (S103) and reads the rack ID (S104). Then, the controller 238 stores the read rack ID on the memory 238a in the controller 238 (S105). On the other hand, when the value of the variable i is not 2 (S102: NO), the process advances to S106.

Next, the controller 238 positions the reading section B1 in front of a holding position i in the sample rack L (S106). Here, when it is detected that the sample container T is held in the holding position i due to the driving of the sections in the reading section B1 as explained with reference to FIGS. 4A and 4B (S107: YES), the controller 238 reads the sample ID of the sample container T which is held in this holding position (S108). On the other hand, when it is detected that no sample container T is held in the holding position i (S107: NO), the process advances to S109.

Next, the controller 238 stores the sample ID and the presence or absence of the sample container T in association with this holding position i on the memory 238a in the controller 238 (S109). When no sample container T is detected in S107, only the presence or absence of the sample container T is stored in S109.

Next, when the value of the variable i is not 5 (S110: NO), 1 is added to the value of the variable i (S111) and the process returns to S102. On the other hand, when the value of the variable i is 5 (S110: YES), the process ends.

Referring to FIG. 15B, the controller 238 of the output unit 23 generates a variable j in the memory 238a in the controller 238 and sets this variable j to 6 (S201). Next, the same process is performed in S202 to S205 as in S106 to S109 of FIG. 15A.

Next, when the value of the variable j is not 10 (S206: NO) in S206, 1 is added to the value of the variable j (S207) and the process returns to S202. On the other hand, when the value of the variable j is 10 (S206: YES), the process ends.

In this manner, the two processes of FIGS. 15A and 15B are performed in parallel, and when both of these two processes end, the rack information is stored as shown in FIG. 14B on the memory 238a in the controller 238 of the output unit 23. The controller 238 transmits the rack information to the transport controller 6 when both the processes of FIGS. 15A and 15B end.

FIG. 16A is a flowchart showing a process of the transport controller 6 in the detection operation of the container detection unit E.

The controller 601 of the transport controller 6 puts the process on hold until the sample rack L reaches the front position of the recovery unit 21 (S21). That is, the controller 601 puts the process on hold until receiving the fact that the sample rack L has been detected by the sensor 214 from the recovery unit 21. The rack ID of the sample rack L is read by the barcode reader 243 just before the sample rack L reaches the front position of the recovery unit 21.

When the sample rack L reaches the front position of the recovery unit 21 (S21: YES), the controller 601 instructs the recovery unit 21 to perform a detection operation by the container detection unit E (S22). When receiving the detection operation instruction, the recovery unit 21 drives the container detection unit E to detect the presence or absence of the sample container T in each holding position in the sample rack L as described above.

FIG. 16B is a view conceptually showing the information which is obtained by the reading operation of the barcode reader 243 and the detection operation of the container detection unit E, that is, the rack ID of the sample rack L and the presence or absence of the sample container T in each holding position in the sample rack L. Hereinafter, the information which is obtained by the reading operation of the barcode reader 243 and the detection operation by the container detection unit E is referred to as "presence or absence information".

As shown in the drawing, according to the presence or absence information in this case, it is recognized that no sample container T is held in the holding positions 2, 4, and 5 in the sample rack L. When obtaining the presence or absence information by the detection operation of the container detection unit E, the recovery unit 21 transmits this presence or absence information to the transport controller 6.

Returning to FIG. 16A, the controller 601 of the transport controller 6 puts the process on hold until receiving the presence or absence information from the recovery unit 21 (S23). When receiving the presence or absence information from the recovery unit 21 (S23: YES), the controller 601 stores this presence or absence information on the hard disk 603 (S24). In addition, the controller 601 stores the date and time at which this presence or absence information is received on the hard disk 603.

Next, the controller 601 reads out the rack information of the sample rack L corresponding to the rack ID of this presence or absence information from the hard disk 603 and compares it with the presence or absence information received in S23. In this manner, the controller 601 determines whether or not there is a sample container T which is detected in the upstream (rear position of the output unit 23) but is not detected in the downstream (front position of the recovery unit 21) (S25). For example, when the rack information of FIG. 14B is compared with the presence or absence information of FIG. 16B, it is recognized that the sample container T in the holding position 2 is detected in the upstream (rear position of the output unit 23), but is not detected in the downstream (front position of the recovery unit 21).

When there is a sample container T which is detected in the upstream but is not detected in the downstream (S25: YES), the controller 601 displays a loss notification screen on the display section 604 (S26). On the other hand, when there is no sample container T which is detected in the upstream but is not detected in the downstream (S25: NO), the process returns to S21.

In this manner, the process of FIG. 16A is repeated for each sample rack L which reaches the front position of the recovery unit 21 in the transport controller 6.

FIG. 16C is a view showing an example of a loss notification screen 800 which is displayed on the display section 604. The loss notification screen 800 includes a recovery state screen button 801 and an OK button 802.

In this case, the loss notification screen 800 displays the fact that a sample container T with a sample ID "R0002" has been lost. Accordingly, a user can identify that the sample container T has been lost between the upstream and the downstream and can specify the lost sample container T. When the recovery state screen button 801 is pushed, a recovery state screen 820 (see FIG. 18B) is displayed. When the OK button 802 is pushed, the loss notification screen 800 is closed.

Figure 17B:
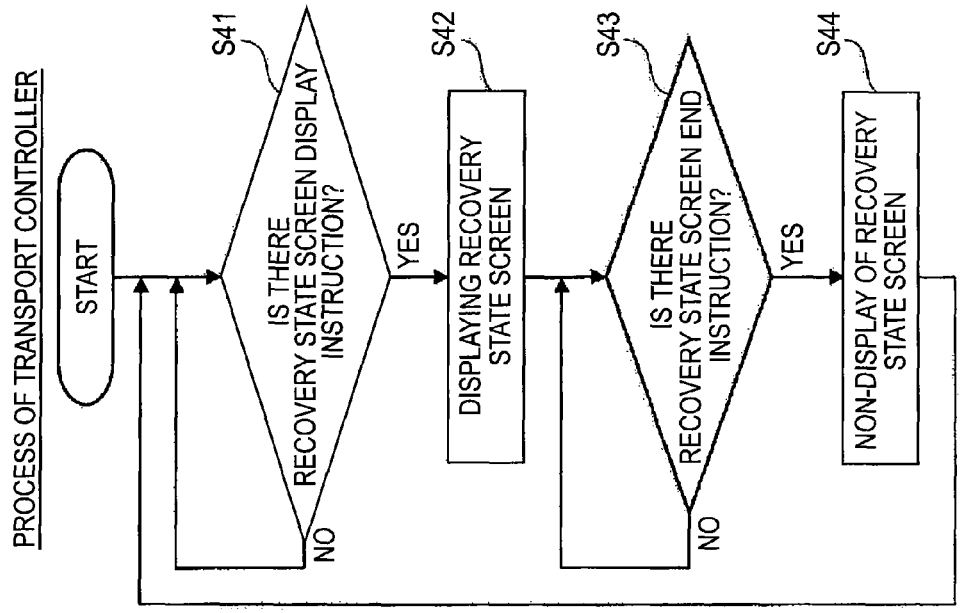
FIG. 17B is a flowchart showing a process related to the display of a recovery state screen by the transport controller according to the embodiment.
Figure 17A:
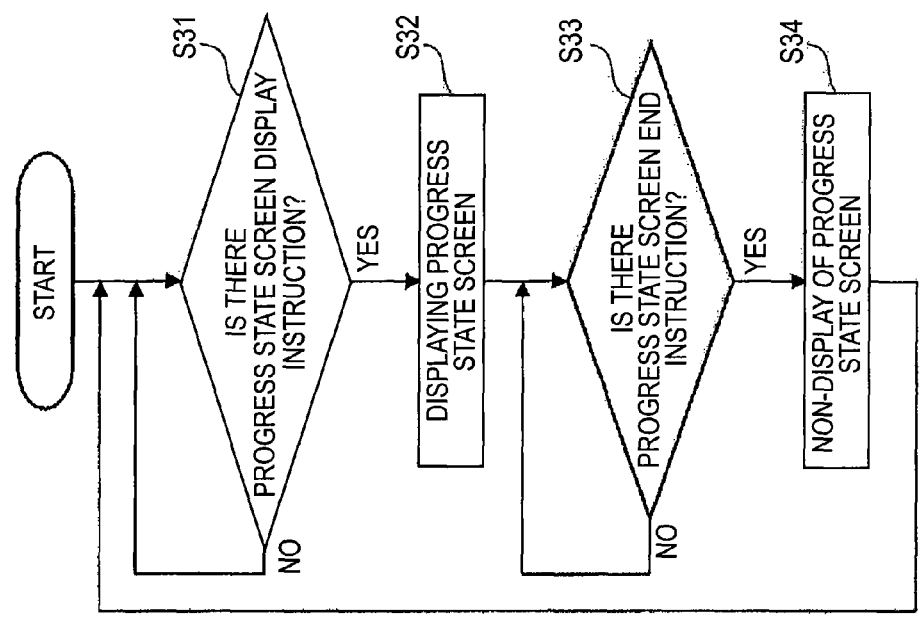
FIG. 17A is a flowchart showing a process related to the display of a progress state screen by the transport controller according to the embodiment.

FIG. 17A is a flowchart showing a process related to the display of a progress state screen by the transport controller 6.

When a progress state screen display instruction is issued (S31: YES), the controller 601 of the transport controller 6 displays a progress state screen 810 (see FIG. 18A) on the display section 604 on the basis of the presence or absence information and the rack information stored on the hard disk 603 (S32). The instruction for displaying the progress state screen 810 is issued when a user pushes a progress state display button (not shown) disposed in the menu of the main screen which is displayed on the display section 604 of the transport controller 6.

FIG. 18A is a view showing an example of the progress state screen 810 which is displayed on the display section 604. The progress state screen 810 includes a progress state display area 811, a scroll bar 812, and an end button 813.

As shown in the drawing, in the progress state display area 811, items showing "sample ID", "date and time of barcode reading in output unit", "state", and "storage date and time" are set. Through the scroll bar 812, all the cases can be displayed in the progress state display area 811. The progress state screen 810 is closed when a user pushes the end button 813 which is disposed in the upper right.

The term "date and time of barcode reading in the output unit" indicates the date and time at which the rack information including the sample ID of the target sample container T is received by the transport controller 6. The term "storage date and time" indicates the date and time at which the presence or absence information including the presence or absence of the sample container T is received by the transport controller 6.

The "date and time of barcode reading in the output unit" and the "storage date and time" may be the date and time at which the target sample container T is subjected to the reading operation by the barcode unit B and the date and time at which the target sample container T is subjected to the detection operation by the container detection unit E, respectively. In this case, the date and time at which each sample container T is subjected to the reading operation and the date and time at which each sample container T is subjected to the detection operation are added to the rack information which is transmitted from the output unit 23 and the presence or absence information which is transmitted from the recovery unit 21, respectively.

The term "state" indicates a current state of the sample container T. When the "state" is "during processing", it is recognized that this sample container T is in a state where the transport controller 6 has received the rack information including the sample ID of this sample container T, but has not yet, however, received the presence or absence information including the presence or absence of this sample container T. That is, it is recognized that this sample container T is subjected to processing between the position of the barcode unit B and the container detection unit E.

When the "state" is "stored", it is recognized that this sample rack T is in a state where the transport controller 6 receives the presence or absence information that the presence or absence of this sample container T is determined as "presence". That is, it is recognized that this sample container T is stored in the recovery unit 21.

When the "state" is "not clear", it is recognized that this sample container T is in a state where the transport controller 6 receives the presence or absence information that the presence or absence of this sample container T is determined as "absence". That is, it is recognized that this sample container T has been lost between the position of the barcode unit B and the container detection unit E.

Returning to FIG. 17A, when an instruction for closing the progress state screen 810 is issued, that is, when a user pushes the end button 813 (S33: YES), the controller 601 of the transport controller 6 does not display the progress state screen 810 which is displayed on the display section 604 (S34).

FIG. 17B is a flowchart showing a process related to the display of a recovery state screen by the transport controller 6.

When an instruction for displaying a recovery state screen is issued (S41: YES), the controller 601 of the transport controller 6 displays the recovery state screen 820 (see FIG. 18B) on the display section 604 on the basis of the presence or absence information and the rack information stored on the hard disk 603 (S42). The instruction for displaying the recovery state screen 820 is issued when a user pushes a recovery state display button (not shown) disposed in the menu of the main screen which is displayed on the display section 604 of the transport controller 6, or the recovery state screen button 801 of the loss notification screen 800 shown in FIG. 16C.

FIG. 18B is a view showing an example of the recovery state screen 820 which is displayed on the display section 604. The recovery state screen 820 includes a recovery state display area 821, a scroll bar 822, and an end button 823.

As shown in the drawing, in the recovery state display area 821, items showing "rack ID" and "sample container recovery state" are set. By the scroll bar 822, all cases can be displayed in the recovery state display area 821. The recovery state screen 820 is closed when a user pushes the end button 823 which is disposed in the upper right.

In the "sample container recovery state", the recovery state of the sample container T in each holding position in the target sample rack L is visually shown in addition to the holding positions in the sample rack L. When there is a sample container T which is detected in the upstream (rear position of the output unit 23) but is not detected in the downstream (front position of the recovery unit 21), the holding position where the lost sample container T was held in the upstream is marked. For example, in the recovery state screen 820 shown in FIG. 18B, it is recognized that the sample container T in the second holding position from the left in a sample rack L with a rack ID "000010" has been lost.

Returning to FIG. 17B, when an instruction for closing the recovery state screen 820 is issued, that is, when a user pushes the end button 823 (S43: YES), the controller 601 of the transport controller 6 does not display the recovery state screen 820 which is displayed on the display section 604 (S44).

As described above, according to this embodiment, the sample ID of the sample container T which is held in the sample rack L is read by the barcode unit B. In addition, the presence or absence of the sample container T in each holding position in the sample rack L is detected by the barcode unit B and the container detection unit E. Accordingly, it is recognized whether or not the sample container T has been lost between the barcode unit B and the container detection unit E, and the lost sample container T can be specified.

In addition, according to this embodiment, the loss notification screen 800 of FIG. 16C is displayed when the sample container T is lost. Accordingly, a user can identify the loss of the sample container T between the barcode unit B and the container detection unit E. In addition, a user can identify whether or not each sample container T has been lost through the display of the progress state screen 810 of FIG. 18A.

Furthermore, due to the recovery state screen 820 of FIG. 18B, a user can intuitively identify from which holding position the sample container T has been lost. That is, a user cannot distinguish whether the sample container T was not held originally or lost in the course of transport by simply actually seeing the sample rack L recovered in the recovery unit 21. A user can intuitively notice the loss of the sample container T since the holding position of the lost sample container T is shown in the recovery state screen 820.

In this embodiment, the loss of the sample container T is detected between the barcode unit B and the container detection unit E, but the loss of the sample container T may be detected on the basis of the presence or absence of the sample container T which is detected by the barcode unit C or D. That is, in the holding position where the barcode unit B detects the sample container T, when the barcode unit C or D detects no sample container T which is held, the loss of the sample container T may be detected as described above.

As described above, the embodiments of the invention have been described, but are not limited to these.

For example, in the above-described embodiments, blood is exemplified as a measurement target. However, urine may be a measurement target. That is, the invention can also be applied to sample processing systems which examine urine and can be further applied to clinical sample processing systems which examine other clinical samples.

In addition, in the above-described embodiments, when the sample container T is lost, the loss notification screen 800 of FIG. 16C is displayed as a recognition process for making a user recognize the fact, but the invention is not limited to this. As the recognition process of making a user recognize the loss of the sample container T, a process of notifying the loss of the sample container T using a lamp, sound or the like, a process of stopping the transport line, a process of stopping the measurement by the measuring unit 41 or the like may be performed. Accordingly, a user can notice the loss of the sample container T and can take a necessary measure while noticing the occurrence of some kind of abnormality and coping with the abnormality.

In addition, in the above-described embodiments, as shown in FIG. 1, the output unit 23 and the recovery unit 21 are disposed on the same side (right side) with respect to the measuring units 41 and the smear preparation apparatus 5.

However, the invention is not limited thereto, and the output unit 23 and the recovery unit 21 may be disposed on the opposite side with respect to the measuring units 41 and the smear preparation apparatus 5. For example, the recovery unit 21 may be disposed on the left side of the smear preparation apparatus 5. Furthermore in this case, as in the above-described embodiments, the loss of the sample container T can be detected by the barcode unit B which is disposed at the output unit 23 and the container detection unit E which is disposed at the recovery unit 21.

In addition, in the above-described embodiments, the rack information is obtained by the barcode unit B and the presence or absence information is obtained by the container detection unit E, but the invention is not limited thereto. The rack information and the presence or absence information may be obtained by the barcode unit B.

FIG. 19A is a view schematically showing a transport route of a sample rack L when the rack information and the presence or absence information are obtained by the barcode unit B. The dotted line represents a transport route of a sample rack L from when the sample rack L is placed in the feeding unit 22 to when the sample rack L is output to the transport unit 31 from the output unit 23. In addition, the broken line represents a transport route of a sample rack L from when the sample rack L is output to the output unit 23 from the transport unit 31 along the recovery line to when the sample rack L is recovered in the recovery unit 21.

Also in this case, as in the above-described embodiments, regarding the sample rack L which is placed in the feeding unit 22, first, the rack information is obtained by the barcode unit B at the rear position of the output unit 23.

Next, the sample rack L which has been subjected to the measurement or smear preparation and output in the rightward direction from the transport unit 31 along the recovery line is positioned at the front position of the feeding unit 22 by the belts 237 and 224 and is pushed backward by a rack pushing mechanism 225 which is disposed in the vicinity of the front position of the feeding unit 22. The sample rack L which is positioned again on the feeding unit 22 is positioned at the rear position of the output unit 23, and only the presence or absence of the sample container T in each holding position in the sample rack L is detected by the barcode unit B. Then, this sample rack L is recovered in the recovery unit 21 through the belts 237, 224, and 213.

In this manner, also in the case in which the rack information and the presence or absence information are obtained by the barcode unit B, the loss of the sample container T can be detected during the period from the first positioning at the barcode unit B to the second positioning at the barcode unit B as described above.

In addition, in the above-described embodiments, the holding state of the sample container T at the rear position of the output unit 23 is compared with the holding state of the sample container T at the front position of the recovery unit 21 and thus the loss of the sample container T is detected. However, the positions where the holding states are compared are not limited thereto.

FIG. 19B is a plan view when reflection type sensors 324 and 325 which are disposed near the supply position of the transport units 31 to 33 are viewed from the upper side. As shown in the drawing, the sensors 324 and 325 are disposed on the upstream side and the downstream side with respect to the supply position, respectively. The sensors 324 and 325 can detect whether or not the sample container T is held ahead thereof (at the back).

In this manner, it is recognized whether or not the sample container T which is held in the sample rack L when passing through the front of the sensor 324 is held when passing through the front of the sensor 325. Accordingly, the loss of the sample container T is detected during the period from when the sample container T is taken into the measuring unit 41 from the position of the sensor 324 and is subjected to the measurement to when the sample container T is positioned at the position of the sensor 325.

As shown in FIG. 19C, a reflection type sensor 326 may be disposed only in front of the supply position. In this case, the sample container T before or after being taken into the measuring unit 41 is detected by the sensor 326.

In addition, in the above-described embodiments, the loss of the sample container T is detected by detecting the presence or absence of the sample container T at time points before and after the supply of the sample container T to the measuring unit 41, but the invention is not limited thereto. The presence or absence of the sample container T may be detected at a place on the upstream side in the transport direction of the sample rack L and at a place on the downstream side in the transport direction of the sample rack L at a time point before the supply of the sample container T in the sample rack L to the measuring unit 41. Accordingly, even at a time point before the supply of the sample container T to the measuring unit 41, the loss of the sample container T in the sample rack L can be detected until the sample container T is transported from a place on the upstream side in the transport direction to a place on the downstream side in the transport direction. Therefore, for example, even when an examination technician of another examination department takes the sample container T from the sample rack L during the transport of the sample rack L, the loss of the sample container T can be rapidly noticed at a time point before the supply of the sample container T to the measuring unit 41.

In addition, in the above-described embodiments, the rack information is obtained by the barcode unit B at the rear position of the output unit 23, but the invention is not limited thereto. The rack information may be obtained by the barcode unit B at the front position of the transport passage 221 of the feeding unit 22.

In addition, in the above-described embodiments, the reading of the sample ID and the detection of the presence or absence of the sample container T are performed in parallel by the barcode unit B, but the invention is not limited thereto. The reading of the sample ID and the detection of the presence or absence of the sample container T may be performed at different positions on the transport route. For example, first, the reading of the sample ID may be performed on the upstream side in the transport route and the detection of the presence or absence of the sample container T may be performed on the downstream side in the transport route.

In addition, the detection of the presence or absence of the sample container T is not limited to the above-described method of detecting the sample container T and may be performed using a transmission type sensor including a light-emitting section and a light-receiving section or a reflection type sensor. In addition, the presence or absence of the sample container T may be detected by bringing a contact member into contact with the sample container T. In addition, a portion of the cap section CP of the sample container T protruding upward from the upper surface of the sample rack L may be picked up and the presence or absence of the sample container T may be detected on the basis of the picked-up image.

In addition, in the above-described embodiments, the sample container T is transported by being held in the sample rack L, but the invention is not limited thereto. The sample container T may be transported by a transport section directly holding the sample container T.

In addition, in the above-described embodiments, inversion stirring of the sample container T, sample dispensing, and the like are performed together in one measuring unit 41. However, only one of inversion stirring of the sample container T, sample dispensing, and the like may be performed in the measuring unit 41.

In addition, in the above-described embodiments, the loss of the sample container T is detected by comparing the rack information which is obtained by the barcode unit B with the presence or absence information which is obtained by the container detection unit E, but the invention is not limited thereto. A sensor which detects the presence or absence of the sample container T may be further added on the transport route.

Figure 20:
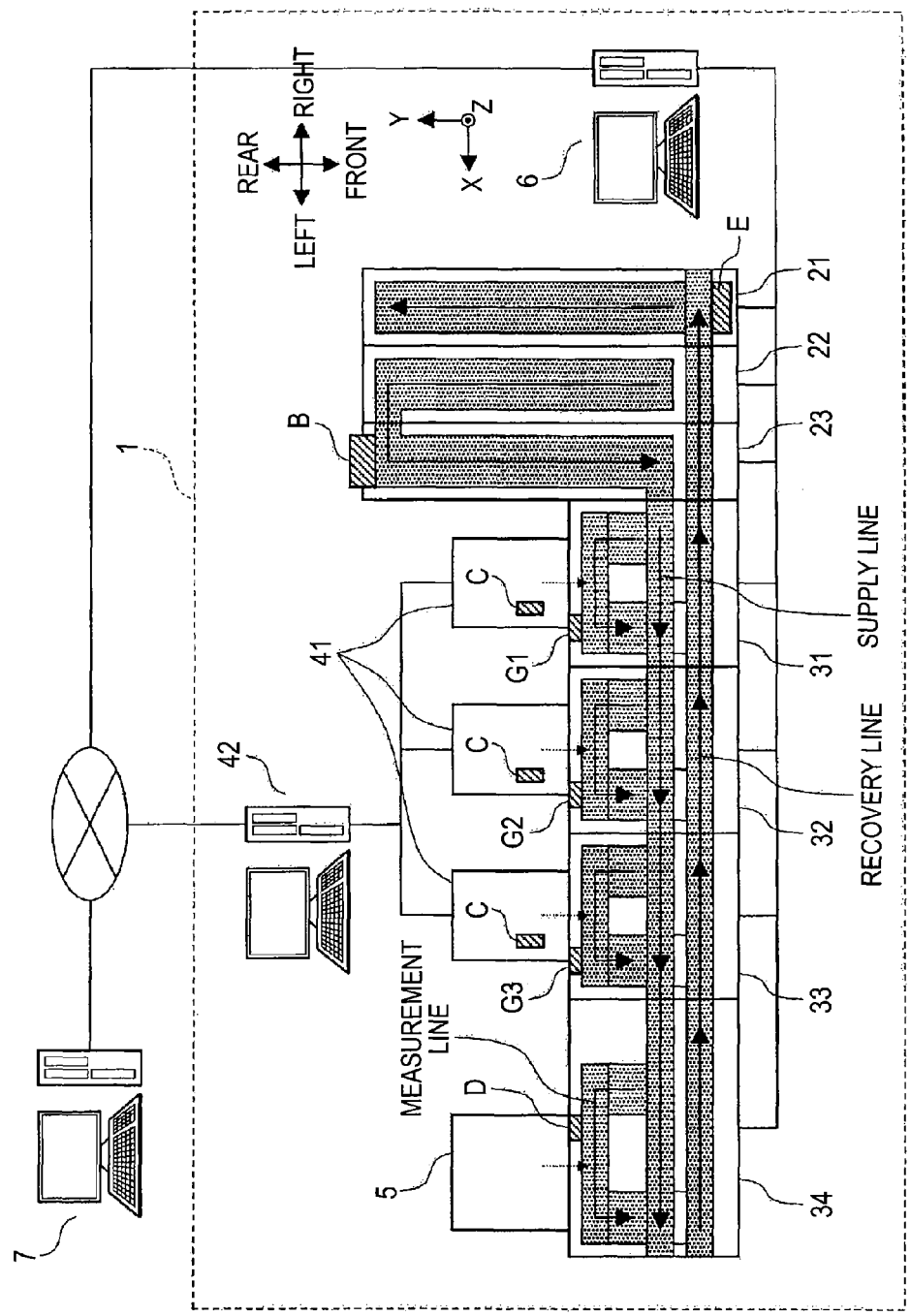
FIG. 20 is a view showing a modified example of the sample processing unit according to the embodiment.

FIG. 20 is a view showing the configuration shown in FIG. 1 with reflection type sensors G1 to G3 added thereto. As shown in the drawing, the sensors G1 to G3 are disposed in the vicinity of the left sides of the rack transport sections 320 of the transport units 31 to 33, respectively.

In this case, in the holding position where the barcode unit B detects the sample container T, when the sensors G1 to G3 detect no sample container T which is held, the loss of the sample container T may be detected as described above.

In this manner, for example, when the sample container T detected by the barcode unit B is not detected by the sensor G1, it is recognized that this sample container T has been lost between the barcode unit B and the sensor G1. In addition, when the sample container T detected by the sensor G2 is not detected by the container detection unit E, it is recognized that this sample container T has been lost between the sensor G2 and the container detection unit E.

In addition, in the above-described embodiments, the rack ID of the sample rack L is read by the barcode reader 243 which is disposed at the front position of the recovery unit 21. In addition, the presence or absence of the sample container T in each holding position in the sample rack L is detected by the container detection unit E, and thus the loss of the sample container T is detected. However, the invention is not limited thereto. For example, a reading mechanism such as the barcode unit B which reads the sample IDs of sample containers T in the sample rack L may be disposed at the front position of the recovery unit 21, whereby when a sample ID read by the barcode unit B is not read by the reading mechanism, the loss of the sample container T with the above sample ID adhered thereto may be notified.

The embodiments of the invention can be appropriately and variously modified within the scope of the technical idea shown in the claims.

What is claimed is:

1. A sample processing apparatus comprising:
a sample processing unit configured to process a sample contained in a sample container;
one or more detectors located to detect the sample container both before and after the sample contained therein is processed by the sample processing unit; and
a controller configured to perform an operation to alert a user if the one or more detectors fail to detect the sample container after the sample processing unit processed the sample in the sample container.

2. The sample processing apparatus of claim 1, wherein as the operation to alert the user, the controller performs an operation to notify the user of a loss of the sample container.

3. The sample processing apparatus of claim 1, further comprising
a transport unit configured to transport the sample container,
wherein the sample processing unit is configured to process the sample in the sample container transported by the transport unit.

4. The sample processing apparatus of claim 3,
wherein the sample processing unit receives the sample container from the transport unit to process the sample in the sample container, and returns the sample container to the transport unit.

5. The sample processing apparatus of claim 4,
wherein the transport unit is configured to transport the sample container by way of the sample processing unit, and
the one or more detectors include a first sample container detector which is located on an upstream side in a transport direction of the sample container with respect to the sample processing unit, and a second sample container detector which is located on a downstream side in the transport direction with respect to the sample processing unit.

6. The sample processing apparatus of claim 5, further comprising:
a supply unit in which the sample container is placed and which supplies the placed sample container to the transport unit; and
a recovery unit configured to recover the sample container from the transport unit after the sample container was transported to the sample processing unit by the transport unit,
wherein the first sample container detector is located at the supply unit, and
the second sample container detector is located at the recovery unit.

7. The sample processing apparatus of claim 3,
wherein the transport unit is configured to transport the sample container through a receiving position at which the sample processing unit receives the sample container from the transport unit and to which the sample processing unit returns the sample container, and
the one or more detectors are one detector which is located at the receiving position to detect the sample container both before and after the sample processing unit receives the sample container at the receiving position.

8. The sample processing apparatus of claim 3,
wherein the transport unit is configured to transport a sample rack capable of holding a plurality of sample containers, and
the sample processing unit is configured to process the sample contained in the sample container in the sample rack transported by the transport unit.

9. The sample processing apparatus of claim 8,
wherein the sample rack has identification information for identifying the sample rack,
the sample rack is capable of holding the plurality of sample containers at a plurality of container holding positions,
the one or more detectors are configured to obtain the identification information from the sample rack and to detect presence or absence of a sample container in each container holding position in the sample rack, and
the controller performs the operation to alert the user if the one or more detectors fail to detect the sample container in the sample rack after the sample processing unit processed the sample in the sample container.

10. The sample processing apparatus of claim 1,
wherein the sample container has identification information for identifying the sample container, the one or more detectors are configured to obtain identification information from the sample container, and the controller performs the operation to alert the user if the one or more detectors fail to obtain the identification information after the sample processing unit processed the sample in the sample container.

11. The sample processing apparatus of claim 1,
wherein the sample processing unit includes a holding unit configured to hold the sample container and a rotation actuator configured to allow the holding unit to rotate in order to stir the sample in the sample container.

12. The sample processing apparatus of claim 1, further comprising
a display,
wherein as the operation to alert the user, the controller shows loss information for informing the user of a loss of the sample container on the display.

13. The sample processing apparatus of claim 12,
wherein the controller shows a screen on the display, the screen displaying a progress state of the processing of the sample in the sample container and the loss information.

14. The sample processing apparatus of claim 8, further comprising:
a display; and
a rack recovery unit configured to recover the sample rack from the transport unit after the sample rack was transported to the sample processing unit by the transport unit,
wherein the controller shows a screen on the display, the screen displaying the sample rack recovered in the rack recovery unit and a container holding position in the sample rack which held a sample container lost from the sample rack.

15. A sample container transporting apparatus for transporting a sample container to a sample processing apparatus for processing a sample in the sample container, comprising:
a transport unit configured to transport the sample container from a first position to a second position;
a first detector located to detect the sample container at the first position;
a second detector located to detect the sample container transported to the second position; and
a controller configured to perform an operation to alert a user if the second detector fails to detect the sample container which was detected by the first detector.

16. The sample container transporting apparatus of claim 15, further comprising
a sample processing apparatus configured to process the sample contained in the sample container transported by the transport unit between the first and second positions.

17. The sample container transporting apparatus of claim 15,
wherein the transport unit is configured to transport a sample rack capable of holding a plurality of sample containers at a plurality of container holding positions, and has rack identification information,
the first detector obtains rack identification information from the sample rack at the first position and detects presence or absence of the sample container in each container holding position in the sample rack,
the second detector obtains the rack identification information from the sample rack at the second position and detects the presence or absence of the sample container in each container holding position in the sample rack, and
the controller performs the operation to alert the user if the second detector fails to detect the sample container in the sample rack, which was detected by the first detector.

18. A sample processing method comprising:
(a) performing an operation of detecting a sample container containing a sample;
(b) processing the sample contained in the sample container detected in the step (a);
(c) performing an operation of detecting the sample container after the step (b); and
(d) performing an operation to alert a user if the step (c) fails to detect the sample container which was detected in the step (a).

19. The sample processing method of claim 18, further comprising:
transporting the sample container from a first position to a second position by a transport unit,
wherein the step (a) is executed at the first position,
the step (b) is executed between the first and second positions, and
the step (c) is executed at the second position.

20. A sample container transporting method of transporting a sample container to a sample processing apparatus for processing a sample in the sample container, comprising:
(a) performing an operation of detecting a sample container at a first position;
(b) transporting the sample container to a second position from the first position by a transport unit;
(c) performing an operation of detecting the sample container transported to the second position; and
(d) performing an operation to alert a user if the step (c) fails to detect the sample container which was detected in the step (a).

* * * * *